United States Patent
Mahne

(10) Patent No.: US 11,723,945 B2
(45) Date of Patent: Aug. 15, 2023

(54) PHARMACEUTICAL COMPOSITION COMPRISING TRYPTOPHAN AND PHYLLOKININ DERIVATIVE FOR USE IN TREATING PSYCHIATRIC AND PSYCHOLOGICAL CONDITIONS

(71) Applicant: Temple Otorongo LLC, Livingston, NJ (US)

(72) Inventor: Chris W. Mahne, Livingston, NJ (US)

(*) Notice: Subject to any disclaimer, the term of this patent is extended or adjusted under 35 U.S.C. 154(b) by 373 days.

(21) Appl. No.: 16/606,984

(22) PCT Filed: Apr. 23, 2018

(86) PCT No.: PCT/US2018/028869
§ 371 (c)(1),
(2) Date: Oct. 21, 2019

(87) PCT Pub. No.: WO2018/200381
PCT Pub. Date: Nov. 1, 2018

(65) Prior Publication Data
US 2021/0275623 A1 Sep. 9, 2021

Related U.S. Application Data

(60) Provisional application No. 62/489,745, filed on Apr. 25, 2017.

(51) Int. Cl.
*A61K 38/00* (2006.01)
*A61K 38/04* (2006.01)
*A61K 47/54* (2017.01)
*A61K 31/405* (2006.01)
*A61K 45/06* (2006.01)

(52) U.S. Cl.
CPC .......... *A61K 38/043* (2013.01); *A61K 31/405* (2013.01); *A61K 45/06* (2013.01); *A61K 47/545* (2017.08)

(58) Field of Classification Search
None
See application file for complete search history.

(56) References Cited

U.S. PATENT DOCUMENTS

| | | |
|---|---|---|
| 4,291,048 A | 9/1981 | Gold |
| 4,335,209 A | 6/1982 | Asai et al. |
| 4,588,687 A | 5/1986 | Tsuchida et al. |
| 4,601,982 A | 7/1986 | Shiio et al. |
| 4,849,408 A | 7/1989 | Sommermeyer et al. |
| 4,870,097 A | 9/1989 | Makovec et al. |
| 5,162,497 A | 11/1992 | Coy et al. |
| 5,275,940 A | 1/1994 | Kino et al. |
| 5,563,052 A | 10/1996 | Katsumata et al. |
| 5,624,828 A | 4/1997 | Katsumata et al. |
| 5,629,202 A | 5/1997 | Su et al. |
| 5,776,740 A | 7/1998 | Hatakeyama et al. |
| 5,776,970 A | 7/1998 | Shechter et al. |
| 6,015,818 A | 1/2000 | Oku et al. |
| 6,096,737 A | 8/2000 | Loder |
| 6,127,389 A | 10/2000 | Oku et al. |
| 6,316,413 B1 | 11/2001 | Dodey et al. |
| 6,921,805 B2 | 7/2005 | Richelson et al. |
| 7,659,304 B2 | 2/2010 | Somei et al. |
| 7,670,619 B2 | 3/2010 | Mihaylov |
| 7,807,629 B1 | 10/2010 | Sharif |
| 7,847,152 B2 | 12/2010 | Widholm |
| 8,198,265 B2 | 6/2012 | Munn et al. |
| 8,344,162 B2 | 1/2013 | Jung et al. |
| 8,569,233 B2 | 10/2013 | Tian et al. |
| 8,735,539 B2 | 5/2014 | Kraynov et al. |
| 8,791,231 B2 | 7/2014 | Miao et al. |
| 8,945,907 B2 | 2/2015 | Ju et al. |
| 9,164,106 B2 | 10/2015 | Schwartz et al. |
| 9,304,135 B2 | 4/2016 | Jung et al. |
| 2012/0108510 A1 | 5/2012 | Young et al. |
| 2012/0283260 A1 | 11/2012 | Combrink et al. |
| 2013/0096050 A1* | 4/2013 | Shandler ............ A61K 38/2278 514/6.9 |
| 2013/0136717 A1 | 5/2013 | Hillmeister et al. |

(Continued)

FOREIGN PATENT DOCUMENTS

WO    2004058258 A1    7/2004

OTHER PUBLICATIONS

Asraf et al. Front. Endocrinol., Apr. 19, 2017. Involvement of the Bradykinin B1 Receptor in Microglial Activation: In Vitro and In Vivo Studies (Year: 2017).*
Viana et al. Kinin B1 receptors mediate depression-like behavior response in stressed mice treated with systemic E. coli lipopolysaccharide. J Neuroinflammation. 2010; 7: 98. (Year: 2010).*
Levitan et al. (J Psychiatry Neurosci 2000;25(4):337-46) Preliminary randomized double-blind placebocontrolled trial of tryptophan combined with fluoxetine to treat major depressive disorder: antidepressant and hypnotic effects (Year: 2000).*
Anatsai et al., "Pharmacological Data on Phyllokinin (Bradykinyl-Isoleucyl-Tyrosine O-Sulphate) and Bradykinyl-Isoleucyl-Tyrosine," Br. J. Pharmacol Chemother. 27: 479-485 (1966), 7 pages.

(Continued)

*Primary Examiner* — Aradhana Sasan
*Assistant Examiner* — Mercy H Sabila
(74) *Attorney, Agent, or Firm* — Ditthavong, Steiner & Mlotkowski

(57) ABSTRACT

Methods for treating psychiatric and psychological diseases or conditions, including depression, by use of L-tryptophan or a derivative or analog thereof and a derivative of phyllokinin are described. The methods can be used together with other agents for treatment of depression or other psychiatric or psychological diseases or conditions. Pharmaceutical compositions comprising at least one of L-tryptophan or a derivative or analog thereof and a derivative of phyllokinin together with a pharmaceutically acceptable excipient are also described. The pharmaceutical compositions can include other therapeutically active agents for the treatment of psychiatric or psychological diseases or conditions such as depression.

8 Claims, No Drawings
Specification includes a Sequence Listing.

(56) References Cited

U.S. PATENT DOCUMENTS

2013/0142815 A1 6/2013 Ganapathy
2015/0342946 A1 12/2015 Bear et al.
2016/0220533 A1 8/2016 Shapiro et al.

OTHER PUBLICATIONS

Lai et al., "A Novel Bradykinin-Related Peptide from Skin Secretions of Toad Bombina maxima and Its Precursor Containing Six Identical Copies of the Final Product," Biochem. Biophys. Res. Commun. 286: 259-263 (2001), retrievd on Nov. 1, 2019, from https://www.sciencedirect.com/science/article/pii/S0006291X01953598, abstract included, 1 page.

Fujita et al., "Isolation and characterization of ovokinin, a bradykinin B1 agonist peptide derived from ovalbumin", Peptides 16: 785-790 (1995), retrieved on Nov. 1, 2019, from https://www.sciencedirect.com/science/article/abs/pii/019697819500054N, abstract included, 1 page.

K. Fukuda et al., "Novel Hypothesis for the Cause of Panic Disorder via the Neuroepithelial Bodies in the Lung," Med. Hypotheses, (2005) 64:1192-1197.

S.K. Bhattacharya et al., "Anxiogenic Activity of Intraventricularly Administered Bradykinin in Rats," J. Psychopharmacol, (1995) 9: 348-354.

Fukuda et al., "The Possible Role of Bradykinin in Mental Disorders," Japan. J. Psychosomatic Med. 44: 829-834 (2004) (provided as English-language abstract), 1 page.

\* cited by examiner

SEQUENCE LISTING

<160> NUMBER OF SEQ ID NOS: 25

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Pro Pro Gly Phe Ser Pro Phe Arg Ile Tyr
1               5                   10

<210> SEQ ID NO 2
<211> LENGTH: 9
<212> TYPE: PRT
<213> ORGANISM: Homo sapiens

<400> SEQUENCE: 2

Arg Pro Pro Gly Phe Ser Pro Phe Arg
1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Pro Pro Gly Phe Ser Pro Phe Arg Trp
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Pro Pro Gly Phe Ser Pro Phe Arg Trp Trp
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Pro Pro Gly Phe Ser Pro Phe Arg Trp Trp Trp
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Pro Pro Gly Phe Ser Pro Phe Arg Trp Trp Trp Trp
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Pro Pro Gly Phe Ser Pro Phe Arg Trp Trp Trp Trp Trp
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Pro Pro Gly Phe Ser Pro Phe Arg Trp Trp Trp Trp Trp Trp
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Pro Pro Gly Phe Ser Pro Phe Arg Trp Trp Trp Trp Trp Trp Trp
1               5                   10                  15

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Pro Pro Gly Phe Ser Pro Phe Arg Trp Trp Trp Trp Trp Trp Trp
1               5                   10                  15

Trp

<210> SEQ ID NO 11
<211> LENGTH: 18
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 11

Arg Pro Pro Gly Phe Ser Pro Phe Arg Trp Trp Trp Trp Trp Trp
1               5                   10                  15

Trp Trp

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Pro Pro Gly Phe Ser Pro Phe Arg Trp Trp Trp Trp Trp Trp
1               5                   10                  15

Trp Trp Trp

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Arg Pro Pro Gly Phe Ser Pro Phe Arg
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (4)..(4)
<223> OTHER INFORMATION: trans-4-hydroxy-L-proline
<220> FEATURE:
<221> NAME/KEY: MOD_RES
<222> LOCATION: (6)..(6)
<223> OTHER INFORMATION: O-(2-thienyl)-alanine
<220> FEATURE:
<221> NAME/KEY: MOD_RES
<222> LOCATION: (8)..(8)
<223> OTHER INFORMATION: (3S)[amino]-5-(carbonylmethyl)-2,3-dihydro-1,5-
      benzothiazepin-4(5H)-one

<400> SEQUENCE: 14

Xaa Arg Pro Xaa Gly Xaa Ser Xaa Arg
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (7)..(7)
<223> OTHER INFORMATION: (3S)[amino]-5-(carbonylmethyl)-2,3-dihydro-1,5-
      benzothiazepin-4(5H)-one

<400> SEQUENCE: 15

Arg Pro Pro Gly Phe Ser Xaa Arg
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: trans-4-hydroxy-L-proline
<220> FEATURE:
<221> NAME/KEY: MOD_RES
<222> LOCATION: (5)..(5)
<223> OTHER INFORMATION: O-(2-thienyl)-alanine
<220> FEATURE:
<221> NAME/KEY: MOD_RES
<222> LOCATION: (8)..(8)
<223> OTHER INFORMATION: 4-methyltyrosine

<400> SEQUENCE: 16

Arg Pro Xaa Gly Xaa Ser Pro Xaa Arg
1               5

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (4)..(4)
<223> OTHER INFORMATION: trans-4-hydroxy-L-proline
<220> FEATURE:
<221> NAME/KEY: MOD_RES
<222> LOCATION: (6)..(6)
<223> OTHER INFORMATION: alpha-(2-indanyl)glycine
<220> FEATURE:
<221> NAME/KEY: MOD_RES
<222> LOCATION: (8)..(8)
<223> OTHER INFORMATION: octahydroindole-2-carboxylic acid
<220> FEATURE:
<221> NAME/KEY: MOD_RES
<222> LOCATION: (9)..(9)
<223> OTHER INFORMATION: alpha-(2-indanyl)glycine

<400> SEQUENCE: 17

Xaa Arg Pro Xaa Gly Xaa Ser Xaa Xaa Arg
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (4)..(4)
<223> OTHER INFORMATION: trans-4-hydroxy-L-proline
<220> FEATURE:
<221> NAME/KEY: MOD_RES
<222> LOCATION: (6)..(6)
<223> OTHER INFORMATION: O-(2-thienyl)-alanine
<220> FEATURE:
<221> NAME/KEY: MOD_RES
<222> LOCATION: (8)..(8)
<223> OTHER INFORMATION: D-1,2,3,4-tetrahydroisoquinoline-3-carbonyl
<220> FEATURE:
<221> NAME/KEY: MOD_RES
<222> LOCATION: (9)..(9)
<223> OTHER INFORMATION: octahydroindole-2-carboxylic acid

<400> SEQUENCE: 18

Xaa Arg Pro Xaa Gly Xaa Ser Xaa Xaa Arg
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Met Lys Arg Pro Pro Gly Phe Ser Pro Phe Arg
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Ser Arg Pro Pro Gly Phe Ser Pro Phe Arg
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: trans-4-hydroxy-L-proline

<400> SEQUENCE: 21

Arg Pro Xaa Gly Phe Ser Pro Phe Arg
1               5

<210> SEQ ID NO 22
<211> LENGTH: 19
<212> TYPE: PRT
<213> ORGANISM: Bombina maxima
```

```
<400> SEQUENCE: 22

Asp Leu Pro Lys Ile Asn Arg Lys Gly Pro Arg Pro Pro Gly Phe Ser
1               5                   10                  15

Pro Phe Arg

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Phe Arg Ala Asp His Phe Pro Leu
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Trp Trp Trp Trp Trp Trp Trp Trp Trp
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Arg, L-Lys, or absent
<220> FEATURE:
<221> NAME/KEY: MOD_RES
<222> LOCATION: (4)..(4)
<223> OTHER INFORMATION: L-Pro or trans-4-hydroxy-L-Pro
<220> FEATURE:
<221> NAME/KEY: MOD_RES
<222> LOCATION: (6)..(6)
<223> OTHER INFORMATION: L-Phe or L-thienylalanine

<400> SEQUENCE: 25

Xaa Arg Pro Xaa Gly Xaa Ser
1               5
```

PHARMACEUTICAL COMPOSITION COMPRISING TRYPTOPHAN AND PHYLLOKININ DERIVATIVE FOR USE IN TREATING PSYCHIATRIC AND PSYCHOLOGICAL CONDITIONS

CROSS-REFERENCE TO RELATED APPLICATION

This application claims the benefit of U.S. Provisional Patent Application Ser. No. 62/489,745 by C. W. Mahne et al., entitled "Pharmaceutical Composition Comprising Tryptophan and Phyllokinin Derivative for Use in Treating Psychiatric and Psychological Conditions," and filed on Apr. 25, 2017, which is incorporated herein in its entirety.

SEQUENCE LISTING

The instant application contains a Sequence Listing which has been submitted electronically in ASCII format and is hereby incorporated by reference in its entirety. Said ASCII copy, created on Feb. 28, 2023, is named P8688US01_SL.txt and is 8,186 bytes in size.

FIELD OF THE INVENTION

The present invention is directed to tryptophan and a phyllokinin derivative for use in treating psychiatric and psychological conditions, including depression, and to pharmaceutical compositions containing tryptophan and a phyllokinin derivative.

BACKGROUND OF THE INVENTION

Psychiatric and psychological conditions, including depression, are extremely common, and are particularly significant in developed countries.

These conditions, including, but not limited to, depression, anxiety, post-traumatic stress disorder (PTSD), substance abuse disorder, schizophrenia, eating disorders, obsessive-compulsive disorder, anxiety disorder, attention deficit hyperactivity, sleep disorders, decreased pleasure and motivation, and dysphoria (e.g., substance-induced or chemotherapy-induced dysphoria), affect a significant proportion of the population in most developed countries. These diseases and conditions are associated with a number of societal problems, including school failure, unemployment, disability, criminal activity, homelessness, and family breakup. In addition, the symptoms of the diseases and conditions are extremely troubling to the sufferers and disrupt lives, sometimes to the point that the sufferers attempt to or actually commit suicide. Although a number of drugs and pharmaceutical compositions are currently in use to treat these diseases and conditions, including monoamine oxidase inhibitors, selective serotonin reuptake inhibitors, tricyclic antidepressants, and antipsychotic agents, including phenothiazines, thioxanthenes, and other agents, these agents are frequently not well tolerated and compliance by patients with therapeutic regimes is frequently poor. A number of significant side effects are associated with many of these drugs, including, but not limited to, epigastric distress, constipation, dizziness, tachycardia, blurred vision, urinary retention, postural hypotension, weakness, fatigue, confusion, delirium, nausea, vomiting, sexual dysfunction, acute dystonia, akathisia, parkinsonism, neuroleptic malignant syndrome, and tardive dyskinesia.

Many pharmacologically active compounds are either obtained directly from naturally occurring plant or animal sources or are chemical modifications of compounds originally obtained from such sources. For example, the psychotropic compound lysergic acid diethylamide (LSD) is a derivative of a compound originally obtained from the ergot fungus. Another example is reserpine, which has anti-psychotic activity and was originally isolated from the plant *Rauwolfia serpentina*. However, there is a need for further exploration of pharmacologically active compounds obtained directly from natural sources or of derivatives of such compounds, including the development of purer preparations of such compounds and the identification of the optimum way to administer and use such compounds, particularly for the treatment of psychiatric and psychological conditions.

SUMMARY OF THE INVENTION

Use of tryptophan and a phyllokinin derivative for the treatment of psychiatric and psychological diseases and conditions meets the needs described above.

One aspect of the present invention is a method for treatment of a psychiatric or psychological disease or condition comprising the step of administering:

(1) a therapeutically effective quantity of tryptophan or a derivative or analog thereof; and (2) a therapeutically effective quantity of a derivative of phyllokinin to a subject suffering from a psychiatric or psychological disease or condition, to treat the disease or condition.

Typically, the psychiatric or psychological condition is depression. In another alternative, the psychiatric or psychological disease or condition can be selected from the group consisting of anxiety, post-traumatic stress disorder, bipolar disorder, substance abuse disorder, eating disorders, obsessive-compulsive disorder, sleep disorders, and dysphoria.

Typically, the tryptophan or derivative or analog thereof is tryptophan. Other alternatives for derivatives and analogs of tryptophan are described.

Typically, the phyllokinin derivative has the structure Arg-Pro-Pro-Gly-Phe-Ser-Pro-Phe-Arg-Trp-Trp-Trp-Trp-Trp-Trp-Trp-Trp-Trp (SEQ ID NO: 11). Other alternatives for phyllokinin derivatives, including peptides with the core structure Arg-Pro-Pro-Gly-Phe-Ser-Pro-Phe-Arg (SEQ ID NO: 2) with different numbers of carboxyl-terminal tryptophan residues, are described. Phyllokinin derivatives with the core structure Arg-Pro-Pro-Gly-Phe-Ser-Pro-Phe-Arg (SEQ ID NO: 2) with from 1 to 10 carboxyl-terminal tryptophan residues are referred to generally herein as phyllotryptokinins. Up to 100 carboxyl-terminal tryptophan residues that are attached to SEQ ID NO: 2 can be included in phyllokinin derivatives according to the present invention. In other alternatives, up to 1000 or up to 100,000 carboxyl-terminal tryptophan residues that are attached to SEQ ID NO: 2 can be included in phyllokinin derivatives according to the present invention. Other phyllokinin derivatives and analogs which can have from 1 to 10 carboxyl-terminal tryptophan residues, up to 100 carboxyl-terminal residues, up to 1000 carboxyl-terminal residues, or up to 100,000 carboxyl-terminal residues, can alternatively be used.

Typically, the phyllokinin derivative is administered in a quantity of from 1 ng/kg to about 100 mg/kg. Preferably, the phyllokinin derivative is administered in a quantity of from about 5 ng/kg to about 75 ng/kg. More preferably, the phyllokinin derivative is administered in a quantity of from about 10 ng/kg to about 50 ng/kg.

Typically, the tryptophan or derivative or analog thereof is administered in a quantity of from about 0.1 mg/kg to about 1000 mg/kg. Preferably, the tryptophan or derivative or analog thereof is administered in a quantity of from about 0.5 mg/kg to about 500 mg/kg. More preferably, the tryptophan or derivative or analog thereof is administered in a quantity of from about 1 mg/kg to about 250 mg/kg.

Typically, the phyllokinin derivative and the L-tryptophan or derivative or analog thereof are administered daily. Typically, the phyllokinin derivative and the L-tryptophan or derivative or analog thereof are administered in one or more pharmaceutical compositions; a single pharmaceutical composition or two separate pharmaceutical compositions can be used.

When the disease or condition being treated is depression, the method can further comprise administration of a therapeutically effective quantity of an additional agent for treatment of depression. The additional agent can be, but is not limited to: a selective serotonin reuptake inhibitor; a serotonin-norepinephrine reuptake inhibitor; a serotonin modulator; a serotonin antagonist and reuptake inhibitor; a norepinephrine reuptake inhibitor; a tricyclic antidepressant; a tetracyclic antidepressant; a monoamine oxidase inhibitor; an atypical antidepressant; or an antidepressant that acts by one or more other mechanisms.

Typically, the therapeutically effective quantity of tryptophan and the therapeutically effective quantity of a derivative of phyllokinin are administered subcutaneously.

Another aspect of the invention is a pharmaceutical composition comprising:

(1) at least one therapeutically active agent for the treatment of a psychiatric or psychological disease or condition, wherein the at least one therapeutically active agent is selected from the group consisting of: (a) a derivative of phyllokinin; (b) L-tryptophan or a derivative or analog thereof; (c) a derivative of phyllokinin and an additional agent for treatment of a psychiatric or psychological disease or condition; (d) L-tryptophan or a derivative or analog thereof and an additional agent for treatment of a psychiatric or psychological disease or condition; (e) a derivative of phyllokinin and L-tryptophan or a derivative or analog thereof; and (f) a derivative of phyllokinin, L-tryptophan or a derivative or analog thereof, and an additional agent for treatment of a psychiatric or psychological disease or condition; and (2) a pharmaceutically acceptable excipient.

Suitable phyllokinin derivatives are as described above, including phyllokinin derivatives referred to herein as phyllotryptokinin. When the L-tryptophan or a derivative or analog thereof is a derivative or analog of L-tryptophan rather than L-tryptophan itself, the derivative or analog of L-tryptophan is as described above.

When a pharmaceutical composition according to the present invention includes an additional agent for treatment of a psychiatric or psychological disease or condition, and the psychiatric or psychological disease or condition is depression, the additional agent is as described above. However, the pharmaceutical composition can be formulated for treatment of other psychiatric or psychological disease or conditions as described above.

Typically, the pharmaceutical composition is formulated for subcutaneous administration. In another alternative, the pharmaceutical composition can be formulated for a route of administration selected from the group consisting of intravenous administration, intraperitoneal, and intramuscular administration.

Yet another aspect of the invention is a kit comprising, separately packaged:

(1) two or more unit doses of L-tryptophan or a derivative or analog thereof;

(2) two or more unit doses of a derivative of phyllokinin; and (3) instructions for use.

DETAILED DESCRIPTION OF THE INVENTION

One aspect of the present invention is a method for treatment of a psychiatric or psychological disease or condition comprising the step of administering: (1) a therapeutically effective quantity of tryptophan or a derivative or analog thereof; and (2) a therapeutically effective quantity of a derivative of phyllokinin, to a subject suffering from a psychiatric or psychological disease or condition, to treat the disease or condition.

Typically, the psychiatric or psychological disease or condition is depression. However, the method described herein can also be used for treatment of other psychiatric or psychological conditions, as described further below.

Typically, the therapeutically effective quantity of tryptophan or a derivative or analog thereof and the therapeutically effective quantity of the derivative of phyllokinin are administered subcutaneously. However, other routes of administration can be used and are described below.

I. Tryptophan and Tryptophan Derivatives and Analogs

The structure of tryptophan (more specifically, L-tryptophan) is shown in Formula (I):

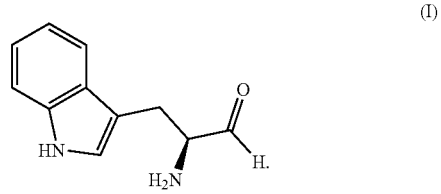

(I)

Biologically, tryptophan is converted to 5-hydroxytryptophan by a reaction catalyzed by the enzyme tryptophan hydroxylase, a reaction which involves the participation of the coenzyme tetrahydrobiopterin. The compound 5-hydroxytryptophan has the structure shown in Formula (II):

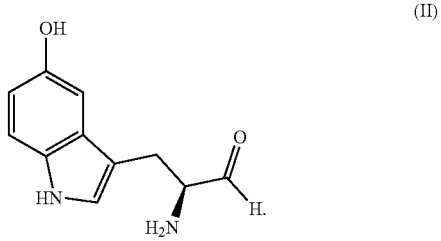

(II)

The intermediate product 5-hydroxytryptophan is then converted to the neurotransmitter serotonin by a reaction catalyzed by the enzyme aromatic amino acid carboxylase. The compound serotonin has the structure shown in Formula (III):

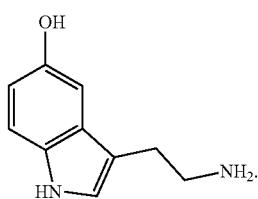

Administration of tryptophan can reverse or minimize serotonin deficiency (U.S. Pat. No. 7,670,619 to Mihaylov).

Serotonin has a number of functions in serotonergic neurons of the central nervous system, including the regulation of mood, sleep, and appetite. Serotonin also has some cognitive functions, including memory and learning. A number of drugs that alter serotonin levels or serotonin metabolism are used in treating depression as well as a number of other types of psychiatric or psychological diseases or conditions, including generalized anxiety disorder or social phobia. These drugs include, but are not limited to, monoamine oxidase inhibitors, tricyclic antidepressants, and selective serotonin reuptake inhibitors.

Tryptophan has significant roles in other biological processes. U.S. Pat. No. 9,164,106 to Schwartz et al. discloses that decreased tryptophan metabolism may be involved in autism spectrum disorders. U.S. Pat. No. 9,304,135 to Jung et al. discloses that alteration of tryptophan metabolism may be associated with stomach cancer. U.S. Pat. No. 8,198,265 to Munn et al. discloses that tryptophan can regulate T-cell mediated immunity. Tryptophan may also be useful in treatment of demyelinating conditions such as multiple sclerosis (U.S. Pat. No. 6,096,737 to Loder). L-tryptophan has also been proposed as useful in a method of inhibiting tumor growth and tumor-associated cachexia (U.S. Pat. No. 4,291,048 to Gold). Tryptophan has also been proposed as useful in the treatment of parasomnias, particularly in children (United States Patent Application Publication No. 2016/0220533 by Shapiro et al.).

In an alternative, L-tryptophan can be replaced with iso-tryptophan, neo-tryptophan, or another tryptophan derivative as described below.

Iso-tryptophan has the structure shown in Formula (IV):

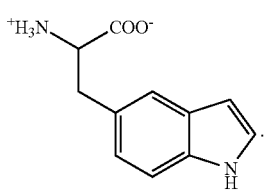

Neo-tryptophan has the structure shown in Formula (V):

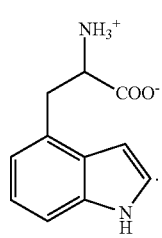

Other tryptophan derivatives (U.S. Pat. No. 6,921,805 to Richelson et al.) have the structure shown in Formula (VI):

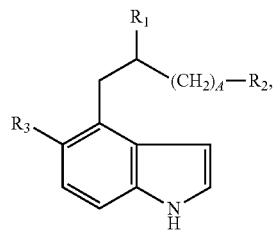

wherein:

(1) $R_1$, $R_2$, and $R_3$ are each independently selected from the group consisting of H, OH, $CH_3$, SH, F, $NH_2$, and COOH; and (2) A is 0, 1, 2, or 3.

Other tryptophan derivatives include, but are not limited to, 6-methyltryptophan, 7-methyltryptophan, and 4-fluorotryptophan (U.S. Pat. No. 7,847,152 to Widholm et al.).

Other tryptophan derivatives include a tryptophan derivative of Formula (VII) (U.S. Pat. No. 7,659,304 to Somei et al.):

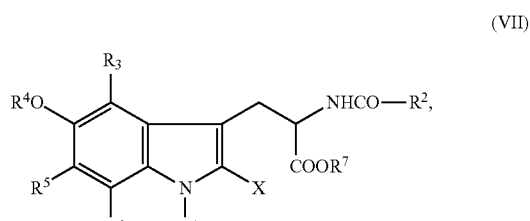

wherein:

(1) X is a halogen atom;

(2) $R^1$ is a hydrogen atom, substituted or unsubstituted $C_1$-$C_6$ alkyl group, substituted or unsubstituted $C_2$-$C_6$ alkenyl group, substituted or unsubstituted $C_2$-$C_6$ alkynyl group, substituted or unsubstituted aromatic group, substituted or unsubstituted aralkyl group, substituted or unsubstituted acyl group, substituted or unsubstituted arylsulfonyl group, substituted or unsubstituted $C_1$-$C_6$ alkylsulfonyl group, substituted or unsubstituted $C_2$-$C_7$ alkoxycarbonyl group, or hydroxyl group;

(3) $R^2$ is a substituted or unsubstituted $C_1$-$C_{21}$ alkyl group;

(4) $R^3$, $R^5$, and $R^6$ are the same or different and are a hydrogen atom or halogen atom;

(5) $R^4$ is a hydrogen atom or substituted or unsubstituted $C_1$-$C_6$ alkyl group; and (6) $R^7$ is a hydrogen atom or substituted or unsubstituted $C_1$-$C_{21}$ hydrocarbon group.

Still other tryptophan derivatives include a tryptophan derivative of Formula (VIII) (U.S. Pat. No. 5,776,970 to Shechter et al.):

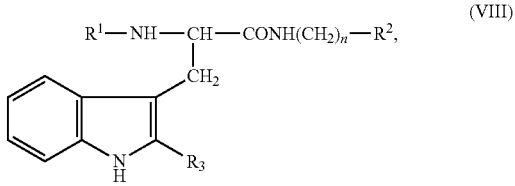

wherein:
(1) $R^1$ is a hydrophobic group;
(2) $R^2$ is —COOH, —SO₃H, or —PO3H;
(3) $R^3$ is H or phenylthio or pyridylthio substituted by one or two $NO_2$ groups; and
(4) n is 1, 2, or 3.

Still other tryptophan derivatives include a tryptophan derivative of Formula (IX) (U.S. Pat. No. 4,870,097 to Makovec et al.):

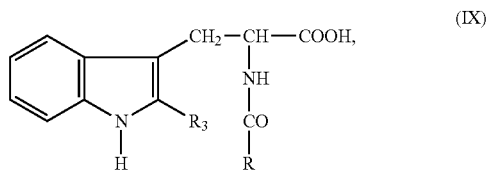

wherein R is selected from: (i) a phenyl group, mono-substituted or di-substituted in the meta position with substituents selected from the group consisting of: (a) halogens; (b) linear or branched alkyl groups containing from 1 to 9 carbon atoms; (c) cyano; and (d) trifluoromethyl; (ii) a benzyloxy group, mono-substituted or di-substituted in the meta position with substituents selected from the group consisting of (a)-(d) in (i); and (iii) a benzhydryloxy group.

Still other tryptophan derivatives include 1-methyltryptophan and α-methyltryptophan (United States Patent Application Publication No. 2013/0142815 by Ganapathy).

Other tryptophan derivatives and analogs are known in the art.

U.S. Pat. No. 8,945,907 to Ju et al. discloses a biosynthetic method for producing L-tryptophan using genetically engineered *Escherichia coli*. U.S. Pat. No. 5,776,740 to Hatakeyama et al. discloses a process for producing L-tryptophan in a single-stage reaction, comprising carrying out an L-tryptophan producing reaction with glycine, formaldehyde and indole as raw materials in an aqueous solution in the presence of microbial cells having serine transhydroxymethylase and microbial cells having tryptophan synthetase or tryptophanase and collecting produced L-tryptophan from the reaction solution. U.S. Pat. No. 5,629,202 to Su et al. discloses a computer-controlled bioreactor system for enzymatic synthesis of L-tryptophan. U.S. Pat. No. 5,624,828 to Katsumata et al. discloses a process for producing L-tryptophan in serine auxotrophic microorganisms. U.S. Pat. No. 5,563,052 to Katsumata et al. discloses a process for producing L-tryptophan using recombinant DNA. U.S. Pat. No. 5,275,940 to Kino et al. discloses a process for producing L-tryptophan using a *Corynebacterium glutamicum* mutant. U.S. Pat. No. 4,601,982 to Shiio et al. discloses a process for producing L-tryptophan using a mutant of the genus *Brevibacterium*. U.S. Pat. No. 4,588,687 to Tsuchida et al. discloses a process for producing L-tryptophan by fermentation using a genetically engineered strain of the genus *Bacillus*. U.S. Pat. No. 4,335,209 to Asai et al. discloses an enzymatic process for producing L-tryptophan comprising reacting indole with serine in the presence of tryptophan synthetase or tryptophanase using a racemizing enzyme to result in the production of L-tryptophan.

II. Phyllokinin and Phyllokinin Derivatives

Phyllokinin is described in A. Anastasi et al., "Pharmacological Data on Phyllokinin (Bradykinyl-Isoleucyl-Tyrosine O-Sulphate) and Bradykinyl-Isoleucyl-Tyrosine," Br. J. Pharmacol. Chemother. 27: 479-485 (1966). Phyllokinin has the structure: Arg-Pro-Pro-Gly-Phe-Ser-Pro-Phe-Arg-Ile-Tyr(HSO₃) (SEQ ID NO: 1).

The phyllokinin derivatives according to the present invention include the following alternatives: (1) Arg-Pro-Pro-Gly-Phe-Ser-Pro-Phe-Arg (SEQ ID NO: 2); (2) Arg-Pro-Pro-Gly-Phe-Ser-Pro-Phe-Arg-Trp (SEQ ID NO: 3); (3) Arg-Pro-Pro-Gly-Phe-Ser-Pro-Phe-Arg-Trp-Trp (SEQ ID NO: 4); (4) Arg-Pro-Pro-Gly-Phe-Ser-Pro-Phe-Arg-Trp-Trp-Trp (SEQ ID NO: 5); (5) Arg-Pro-Pro-Gly-Phe-Ser-Pro-Phe-Arg-Trp-Trp-Trp-Trp (SEQ ID NO: 6); (6) Arg-Pro-Pro-Gly-Phe-Ser-Pro-Phe-Arg-Trp-Trp-Trp-Trp-Trp (SEQ ID NO: 7); (7) Arg-Pro-Pro-Gly-Phe-Ser-Pro-Phe-Arg-Trp-Trp-Trp-Trp-Trp-Trp (SEQ ID NO: 8); (8) Arg-Pro-Pro-Gly-Phe-Ser-Pro-Phe-Arg-Trp-Trp-Trp-Trp-Trp-Trp-Trp (SEQ ID NO: 9); (9) Arg-Pro-Pro-Gly-Phe-Ser-Pro-Phe-Arg-Trp-Trp-Trp-Trp-Trp-Trp-Trp-Trp (SEQ ID NO: 10); (10) Arg-Pro-Pro-Gly-Phe-Ser-Pro-Phe-Arg-Trp-Trp-Trp-Trp-Trp-Trp-Trp-Trp-Trp (SEQ ID NO: 11); and (12) Arg-Pro-Pro-Gly-Phe-Ser-Pro-Phe-Arg-Trp-Trp-Trp-Trp-Trp-Trp-Trp-Trp-Trp-Trp (SEQ ID NO: 12). Phyllokinin derivatives with the core structure Arg-Pro-Pro-Gly-Phe-Ser-Pro-Phe-Arg (SEQ ID NO: 2) with from 1 to 10 carboxyl-terminal tryptophan residues, specifically SEQ ID NO: 3 through SEQ ID NOL 12, are referred to generally herein as phyllotryptokinins. Additionally, the phyllokinin derivatives according to the present invention can include homologs of the peptides described above as SEQ ID NO: 3 to SEQ ID NO: 12 with from 11 to 100 carboxyl-terminal tryptophan residues, such as 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86. 87, 88, 89, 90, 91, 92, 93, 94, 95, 96, 97, 98, 99, or 100 carboxyl-terminal tryptophan residues. In other alternatives, up to 1000 tryptophan residues can be attached at the carboxyl-terminus of SEQ ID NO: 2, such as 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 tryptophan residues, or any intermediate number of tryptophan residues. In still other alternatives, from 1000 up to 100,000 tryptophan residues can be attached at the carboxyl-terminus of SEQ ID NO: 2, such as 2000, 3000, 4000, 5000, 6000, 7000, 8000, 9000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 46,000, 47,000, 48,000, 49,000, 50,000, 51,000, 52,000, 53,000, 54,000, 55,000, 56,000, 57,000, 58,000, 59,000, 59,000, 60,000, 61,000, 62,000, 63,000, 64,000, 65,000, 66,000, 67,000, 68,000, 69,000, 70,000, 71,000, 72,000, 73,000, 74,000, 75,000, 76,000, 77,000, 78,000, 79,000, 80,000, 81,000, 82,000, 83,000, 84,000, 85,000, 86,000, 87,000, 88,000, 89,000, 90,000, 91,000, 92,000, 93,000, 94,000, 95,000, 96,000, 97,000, 98,000, 99,000, or 100,000 tryptophan residues, or any intermediate number of tryptophan residues. In some cases, it may be desirable to use a large number of carboxyl-terminal tryptophan residues to avoid possible adverse effects arising from an overdose of bradykinin.

SEQ ID NO. 2, above, is identical with bradykinin. Bradykinin is an inflammatory mediator that causes blood vessels to dilate and therefore causes blood pressure to fall. Bradykinin dilates blood vessels by the release of prostacyclin, nitric oxide, and endothelium-derived hyperpolarizing factor. Bradykinin also causes constriction of non-vascular smooth muscle in the bronchus and gut, increases vascular permeability, and is also involved in the mechanism of pain. However, bradykinin, and the other peptides described above as SEQ ID NO: 3 to SEQ ID NO: 12, have not been shown to have pharmacological activity for the treatment of psychiatric or psychological diseases or conditions.

Peptides having bradykinin-like activity are described in U.S. Pat. No. 7,807,629 to Sharif, including Lys-Arg-Pro-Pro-Gly-Phe-Ser-Pro-Phe-Arg (SEQ ID NO: 13); H-D-Arg-Arg-Pro-Hyp-Gly-Thi-Ser-D-BT-Arg-OH (SEQ ID NO: 14); H-Arg-Pro-Pro-Gly-Phe-Ser-D-BT-Arg-OH (SEQ ID NO: 15); H-Arg-Pro-Hyp-Gly-Thi-Ser-Pro-4-Me-Tyrψ(CH$_2$NH)-Arg-OH (SEQ ID NO: 16) (RMP-7 or labradimil); D-Arg-Arg-Pro-Hyp-Gly-Igl-Ser-Oic-Igl-Arg-TFA (SEQ ID NO: 17) (B9972); H-D-Arg-Arg-Pro-Hyp-Gly-Thi-Ser-D-Tic-Oic-Arg-OH (SEQ ID NO: 18) (Icatibant); Met-Lys-Arg-Pro-Pro-Gly-Phe-Ser-Pro-Phe-Arg (SEQ ID NO: 19); Ile-Ser-Arg-Pro-Pro-Gly-Phe-Ser-Pro-Phe-Arg (SEQ ID NO: 20); or Arg-Pro-Hyp-Gly-Phe-Ser-Pro-Phe-Arg (SEQ ID NO: 21). In the compounds of SEQ ID NO: 13 to SEQ ID NO: 21, D is D configuration of amino acid; (D-BT) is (3S)[amino]-5-(carbonylmethyl)-2,3-dihydro-1,5-benzothiazepin-4(5H)-one; Hyp is trans-4-hydroxy-L-proline; Igl is α-(2-indanyl)glycine; Oic is octahydroindole-2-carboxylic acid; Thi is O-(2-thienyl)-alanine; Tic is L-1,2,3,4-tetrahydroisoquinoline-3-carbonyl; TFA is trifluoroacetic acid; and CH$_2$NH denotes a reduced peptide bond between the 4-methyltyrosine and arginine amino acids.

Maximakinin, also known as bombinakinin M, has the amino acid sequence Asp-Leu-Pro-Lys-Ile-Asn-Arg-Lys-Gly-Pro-Arg-Pro-Pro-Gly-Phe-Ser-Pro-Phe-Arg (SEQ ID NO: 22) and is described in U.S. Pat. No. 8,614,187 to Shaw et al. Bombinakinin has been isolated from the Chinese red belly toad *Bombina maxima* (R. Lai et al., "A Novel Bradykinin-Related Peptide from Skin Secretions of Toad *Bombina maxima* and Its Precursor Containing Six Identical Copies of the Final Product," *Biochem. Biophys. Res. Commun.* 286: 259-263 (2001)).

Ovokinin has the amino acid sequence Phe-Arg-Ala-Asp-His-Phe-Pro-Leu (SEQ ID NO: 23) (H. Fujita et al., "Isolation and Characterization of Ovokinin, a Bradykinin B1 Agonist Peptide Derived from Ovalbumin," *Peptides* 16: 785-790 (1995).

Additionally, within the scope of the invention are peptides derived from the peptides of SEQ ID NO: 13 to SEQ ID NO: 23 by the addition of from 1 to 100 tryptophan residues at their carboxyl-termini. In other alternatives, within the scope of the invention are peptides derived from the peptides of SEQ ID NO: 13 to SEQ ID NO: 23 by the addition of up to 1000 or up to 100,000 tryptophan residues at their carboxyl-termini, as described above for peptides derived from SEQ ID NO: 2 by the addition of tryptophan residues at their carboxyl-termini.

Additional bradykinin analogs are disclosed in U.S. Pat. No. 6,316,413 to Dodey et al.; U.S. Pat. No. 6,127,389 to Oku et al.; U.S. Pat. No. 6,015,818 to Oku et al.; and 5,162,497 to Coy et al.; and in United States Patent Application Serial Nos. 2013/0136717 by Hillmeister et al.; and 2012/0283260 by Combrink et al.

U.S. Pat. No. 6,316,413 to Dodey et al. discloses bradykinin analogs of Formula (X) (SEQ ID NO: 25):

(X)

H—A$_1$-Arg-Pro-A$_2$-Gly-A$_3$-Ser-HN—[structure with X, Y, CH$_2$—CO—Arg-OH]

wherein:
(1) A$_1$ is a single bond, D-Arg, or L-Lys;
(2) A$_2$ is L-Pro or trans-4-hydroxy-L-Pro;
(3) A$^3$ is L-Phe or L-thienylalanine;
(4) Y is a hydrogen atom or C$_1$-C$_3$ alkyl; and
(5) X is a sulfur or oxygen atom.

Other bradykinin analogs are known in the art and can be used as phyllokinin derivatives in methods and compositions according to the present invention.

Phyllokinin (SEQ ID NO: 1) is hydrolyzed in the body to produce bradykinin (SEQ ID NO: 2), a potent vasodilator. A preferred phyllokinin derivative according to the present invention, Arg-Pro-Pro-Gly-Phe-Ser-Pro-Phe-Arg-Trp-Trp-Trp-Trp-Trp-Trp-Trp-Trp-Trp (SEQ ID NO: 11); is expected to be hydrolyzed in the body to produce: (i) bradykinin; and (ii) Trp-Trp-Trp-Trp-Trp-Trp-Trp-Trp-Trp (SEQ ID NO: 24).

Methods for synthesis of peptides and polypeptides are known in the art. Typically, peptides or polypeptides are synthesized by solid-phase synthesis. In one commonly used method, small porous beads are treated with functional units ("linkers") on which peptide chains can be built. The peptide will remain covalently attached to the bead until cleaved from it by a reagent such as anhydrous hydrogen fluoride or trifluoroacetic acid. The peptide is thus "immobilized" on the solid-phase and can be retained during a filtration process while liquid-phase reagents and by-products of synthesis are flushed away. The general principle of solid-phase peptide synthesis is one of repeated cycles of deprotection-wash-coupling-wash. The free N-terminal amine of a solid-phase attached peptide is coupled (see below) to a single N-protected amino acid unit. This unit is then deprotected, revealing a new N-terminal amine to which a further amino acid may be attached. The superiority of this technique partially lies in the ability to perform wash cycles after each reaction, removing excess reagent with all of the growing peptide of interest remaining covalently attached to the insoluble resin. Solid-phase peptide synthesis proceeds in a carboxyl-terminal to amino-terminal fashion, unlike in vivo protein biosynthesis occurring on ribosomes. Various solid supports can be employed, including gel-type supports, surface-type supports, and composites. Gel-type supports, the most frequently used, are highly solvated polymers with an equal distribution of functional groups, and include polystyrene (styrene cross-linked with 1-2% divinylbenzene), polyacrylamide (hydrophilic alternative to polystyrene), polyethylene glycol (PEG) (PEG-polystyrene (PEG-PS) is more stable than polystyrene and spaces the site of synthesis from the polymer backbone), and PEG-based supports composed of a PEG-polypropylene glycol network or PEG with polyamide or polystyrene. Generally, in solid-phase synthesis, it is necessary to protect the α-amino group of the newly added amino acid; the most frequently used protecting groups for the α-amino group are tert-butyloxycarbonyl (t-Boc) and 9H-fluoren-9-ylmethoxycarbonyl (Fmoc). In some cases, the amino acids to be added have reactive side chains, which can include additional amino groups, such as in lysine, or additional carboxyl groups, such as in aspartic acid or glutamic acid, and such reactive side groups must also be protected during peptide or polypeptide synthesis, generally employing protecting groups based on the benzyl or tert-butyl moieties. These protecting groups are generally removed by acid after the completion of the peptide or polypeptide synthesis. For coupling the peptides, the carboxyl group is generally activated, typically with carbodiimides or triazoles. For longer peptides or polypeptides, shorter fragments can be synthesized and coupled by fragment condensation; alternatively, longer peptides or polypeptides can be formed by chemical ligation, such as by use of a peptide thioester that reacts with a terminal cysteine residue. Other synthesis and coupling methods are known in the art.

III. Routes, Methods, Quantities, and Durations of Administration

Preferably, the phyllokinin derivative and the L-tryptophan or derivative or analog thereof are administered subcutaneously. However, alternative routes of administration are possible, including intravenous, intraperitoneal, and intramuscular administration.

The phyllokinin derivative and the L-tryptophan or derivative or analog thereof can be administered as pure compounds. However, it is generally preferred to administer them as pharmaceutical compositions. When multiple therapeutic agents are administered, each therapeutic agent can be administered separately, or two or more therapeutic agents can be administered in a single pharmaceutical composition. When the agents are administered separately, either one or both of the agents can be administered as pure compounds or in a pharmaceutical composition. Further details for the preparation and use of pharmaceutical compositions are described below.

Typically, the quantities of the therapeutic agents administered are from 1 ng/kg to about 100 mg/kg for the phyllokinin derivative and from about 0.1 mg/kg to about 1000 mg/kg for the L-tryptophan or derivative or analog thereof. Preferably, the quantities of the therapeutic agents administered are from about 5 ng/kg to about 75 ng/kg for the phyllokinin derivative and from about 0.5 mg/kg to about 500 mg/kg for the L-tryptophan or derivative or analog thereof. More preferably, the quantities of the therapeutic agents administered are from about 10 ng/kg to about 50 ng/kg for the phyllokinin derivative and from about 1 mg/kg to about 250 mg/kg for the L-tryptophan or derivative or analog thereof.

Typically, the phyllokinin derivative and the L-tryptophan or derivative or analog thereof are administered daily. In other alternatives, the phyllokinin derivative and the L-tryptophan or derivative or analog thereof can be administered, for example, three times daily, twice daily, once every two days, once every three days, once every week, once every two weeks, once every three weeks, once every month, or at other intervals. It is not necessary that the phyllokinin derivative and the L-tryptophan or derivative or analog thereof be administered on the same schedule; they may be administered on different schedules. It will also be appreciated that the actual dosages of the phyllokinin derivative and the L-tryptophan or derivative or analog thereof will vary according to: the particular agents being used; the makeup of a pharmaceutical composition or compositions if the agents are administered in one or more pharmaceutical compositions; the mode of administration; the particular psychiatric or psychological condition being treated; the severity of the particular psychiatric or psychological condition being treated; the response to treatment; other health considerations affecting the individual being treated; the age, weight, condition, general health and prior medical history of the subject being treated; and pharmacokinetic factors such as liver and kidney function that affect the rate of metabolism and excretion of the agents administered. Methods for determining optimal dosages are described in the art, e.g., Remington: *The Science and Practice of Pharmacy*, Mack Publishing Co., 20$^{th}$ ed., 2000.

The progress of treatment can be monitored by conventional screening methods. When the psychiatric or psychological condition being treated is depression, screening is generally performed by interviews with the patient to determine the existence of symptoms such as sadness, loss of interest in major life activities including work, relationships, and hobbies, sleep disturbances, feelings of worthlessness or inadequacy, self-medication with non-prescription drugs or alcohol, and suicidal thoughts. Other screening methods can be used for other psychiatric or psychological conditions.

IV. Psychiatric and Psychological Diseases and Conditions

Typically, the psychiatric or psychological disease or condition being treated is depression. As used herein, the term "depression" includes major depression and minor depression. However, methods and compositions disclosed herein may also be used for the treatment of other psychiatric or psychological diseases and conditions, including, but not limited to, anxiety, post-traumatic stress disorder, bipolar disorder, substance abuse disorder, eating disorders, obsessive-compulsive disorder, sleep disorders, and dysphoria.

V. Additional Agents Usable for Treatment of Depression

When the phyllokinin derivative and the L-tryptophan or the derivative or analog thereof are administered to treat depression, another agent known in the art as usable for treatment of depression can also be administered in a therapeutically effective quantity.

These additional agents are generally classified in a number of categories in the art. These categories are not exclusive, and a number of additional agents suitable for use in methods according to the present invention can be considered to be in more than one of these categories according to different aspects of their mechanisms of action.

One category of agents known as usable for the treatment of depression is the selective serotonin reuptake inhibitors (SSRIs). Selective serotonin reuptake inhibitors include, but are not limited to, citalopram, excitalopram, fluoxetine, fluvoxamine, paroxetine, sertraline, indalpine, zimelidine, cericlamine, and panuramine.

Another category of agents known as usable for the treatment of depression is the serotonin-norepinephrine reuptake inhibitors. Serotonin-norepinephrine reuptake inhibitors include, but are not limited to, venlafaxine, sibutramine, duloxetine, atomoxetine, desvenlafaxine, milnacipran, and levomilnacipran.

Yet another category of agents known as usable for the treatment of depression is the serotonin modulators. Serotonin modulators include, but are not limited to, vortioxetine and vilazodone.

Yet another category of agents known as usable for the treatment of depression is the serotonin antagonists and reuptake inhibitors. Serotonin antagonists and reuptake inhibitors include, but are not limited to, etoperidone, lorpiprazole, lubazodone, mepiprazole, nefazodone, and trazodone.

Yet another category of agents known as usable for the treatment of depression is the norepinephrine reuptake inhibitors. Norepinephrine reuptake inhibitors include, but are not limited to, amedalin, CP-39,332 (1,2,3,4-tetrahydro-N-methyl-4-phenyl-2-naphthalenamine), daledalin, edivoxetine, esreboxetine, lortalamine, nisoxetine, reboxetine, talopram, talsupram, tandamine, viloxazine, buproprion, ciclazindole, manifaxine, maprotiline, radafaxine, tapentadol, and teniloxazine.

Still another category of agents known as usable for the treatment of depression is the tricyclic antidepressants. Tricyclic antidepressants include, but are not limited to, amitriptyline, butriptyline, clompramine, desipramine, dolesupin, doxepin, imipramine, iprindole, lofepramine, nortriptyline, protriptyline, and trimipramine.

Still another category of agents known as usable for the treatment of depression is the tetracyclic antidepressants. Tetracyclic antidepressants include, but are not limited to, mianserin, mirtazapine, pirlindole, setiptiline, aptazapine, esmirtazapine, metralindole, and oxprotiline.

Still another category of agents known as usable for the treatment of depression is the monoamine oxidase inhibitors. Monoamine oxidase inhibitors include, but are not limited to, isocarboxazid, nialamide, phenelzine, hydracarbazide, tranylcypromine, bifemelane, moclobemide, toloxatone, rasagline, selegiline, benmoxin, iproclozide, iproniazid, mebanazine, octamoxin, pheniprazine, phenoxypropazine, pivalylbenzhydrazine, safrazine, caroxazone, and minaprine.

Still another category of agents known as usable for the treatment of depression is the atypical antidepressants. Atypical antipsychotics include, but are not limited to, amisulpride, lurasidone, and quetiapine.

Still another category of agents known as usable for the treatment of depression is the antidepressants that act by one or more other mechanisms. Antidepressants that act by one or more other mechanisms include, but are not limited to, agomelatine, tandospirone, α-methyltryptamine, etryptamine, indeloxazine, medifoxamine, nomifensine, oxaflozane, and pivagabine.

Still other antidepressant agents known in the art can be used in combination with L-tryptophan or a derivative or analog thereof and phyllokinin derivative.

VI. Conservative Amino Acid Substitutions and Incorporation of Non-Naturally-Occurring Amino Acid Residues In peptides and molecules including peptide moieties according to the present invention as described above, one or more conservative amino acid substitutions can be made provided that the pharmacological activity of the original peptide or molecule including a peptide moiety is substantially retained. As used herein, the term "substantially retained" means that at least 50% of the original pharmacological activity is retained on an equimolar basis. Typically, at least 75% of the original pharmacological activity is retained on an equimolar basis. Preferably, at least 90% of the original pharmacological activity is retained on an equimolar basis.

Conservative amino acid substitutions are well known in the art. More specifically, in a peptide or protein, suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g. Watson et al. Molecular Biology of the Gene, 4th Edition, 1987, Benjamin/Cummings, p. 224). In particular, such a conservative variant has a modified amino acid sequence, such that the change(s) do not substantially alter the peptide's (the conservative variant's) secondary or tertiary structure and/or activity, specifically phyllokinin-like activity in this context. Conservative amino acid substitution generally involves substitutions of amino acids with residues having similar properties (e.g., acidic, basic, positively or negatively charged, polar or non-polar, or other similar properties such as aromaticity) such that the substitutions of even critical amino acids do not substantially alter structure and/or activity. Conservative substitution tables providing functionally similar amino acids are well known in the art. For example, one exemplary guideline to select conservative substitutions includes (original residue followed by exemplary substitution): Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu. An alternative exemplary guideline uses the following six groups, each containing amino acids that are conservative substitutions for one another: (1) alanine (A or Ala), serine (S or Ser), threonine (T or Thr); (2) aspartic acid (D or Asp), glutamic acid (E or Glu); (3) asparagine (N or Asn), glutamine (Q or Gln); (4) arginine (R or Arg), lysine (K or Lys); (5) isoleucine (I or Ile), leucine (L or Leu), methionine (M or Met), valine (V or Val); and (6) phenylalanine (F or Phe), tyrosine (Y or Tyr), tryptophan (W or Trp); (see also, e.g., Creighton (1984) Proteins, W. H. Freeman and Company; Schulz and Schimer (1979) Principles of Protein Structure, Springer-Verlag). One of skill in the art will appreciate that the above-identified substitutions are not the only possible conservative substitutions. For example, for some purposes, one may regard all charged amino acids as conservative substitutions for each other whether they are positive or negative.

In some cases, non-naturally occurring amino acids can be incorporated into phyllokinin derivatives; some examples are described above. The incorporation of non-naturally occurring amino acids is described in U.S. Pat. No. 8,569,233 to Tian et al.; U.S. Pat. No. 8,735,539 to Kraynov et al.; and U.S. Pat. No. 8,791,231 to Miao et al., all incorporated herein by this reference. Methods for accomplishing such incorporation of non-naturally occurring amino acids are known in the art.

Accordingly, as used herein, the term "derivative of phyllokinin" without further qualification refers to any of: (1) any peptide of SEQ ID NO: 1 to SEQ ID NO: 23; (2) a homolog of any of the peptides described above as SEQ ID NO: 3 to SEQ ID NO: 12 with from 11 to 100 carboxyl-terminal tryptophan residues; (3) a peptide derived from the peptides of SEQ ID NO: 13 to SEQ ID NO: 23 by the addition of from 1 to 100 tryptophan residues at its carboxyl-terminus; (4) a peptide derived from (1), (2), or (3) by the replacement of one or more amino acids therein with one or more conservative amino acid substitutions; or (5) a bradykinin analog or derivative as described herein with phyllokinin activity, including a bradykinin analog or derivative including a non-peptide moiety.

VII. Optional Substitutions in Small Molecules, Salts, Solvates, Tautomers, Prodrugs, Polymorphs, and Other Alternative Forms In some cases, optional substitutions can be made in small molecules or non-peptide portions of molecules including both peptide and non-peptide portions provided that the pharmacological activity of the original peptide or molecule including a peptide moiety is substantially retained. As used herein, the term "substantially retained" means that at least 50% of the original pharmacological activity is retained on an equimolar basis. Typically, at least 75% of the original pharmacological activity is retained on an equimolar basis. Preferably, at least 90% of the original pharmacological activity is retained on an equimolar basis. In general, for optional substituents at saturated carbon atoms such as those that are part of the structures of the compounds described above, the following substituents can be employed: $C_6$-$C_{10}$ aryl, heteroaryl containing 1-4 heteroatoms selected from N, O, and S, $C_1$-$C_{10}$ alkyl, $C_1$-$C_{10}$ alkoxy, cycloalkyl, F, amino ($NR^1R^2$), nitro, —SR, —S(O)R, —S($O_2$)R, —S($O_2$)$NR^1R^2$, and —$CONR^1R^2$, which can in turn be optionally substituted. Further descriptions of potential optional substituents are provided below.

Optional substituents as described above that are within the scope of the present invention do not substantially affect the activity of the resulting analog or derivative or the stability of the analog or derivative, particularly the stability of the analog or derivative when incorporated into a pharmaceutical composition. Definitions for a number of common groups that can be used as optional substituents are provided below; however, the omission of any group from these definitions cannot be taken to mean that such a group cannot be used as an optional substituent as long as the chemical and pharmacological requirements for an optional substituent are satisfied. The introduction of an optional substituent does not interfere with the activity of the compound in which the optional substituent is included or with the activity of any additional therapeutically active agent included in a pharmaceutical composition according to the present invention as described below.

As used herein, the term "alkyl" refers to an unbranched, branched, or cyclic saturated hydrocarbyl residue, or a combination thereof, of from 1 to 12 carbon atoms that can be optionally substituted; the alkyl residues contain only C and H when unsubstituted. Typically, the unbranched or branched saturated hydrocarbyl residue is from 1 to 6 carbon atoms, which is referred to herein as "lower alkyl." When the alkyl residue is cyclic and includes a ring, it is understood that the hydrocarbyl residue includes at least three carbon atoms, which is the minimum number to form a ring. As used herein, the term "alkenyl" refers to an unbranched, branched or cyclic hydrocarbyl residue having one or more carbon-carbon double bonds. As used herein, the term "alkynyl" refers to an unbranched, branched, or cyclic hydrocarbyl residue having one or more carbon-carbon triple bonds; the residue can also include one or more double bonds. With respect to the use of "alkenyl" or "alkynyl," the presence of multiple double bonds cannot produce an aromatic ring. As used herein, the terms "hydroxyalkyl," "hydroxyalkenyl," and "hydroxyalkynyl," respectively, refer to an alkyl, alkenyl, or alkynyl group including one or more hydroxyl groups as substituents; as detailed below, further substituents can be optionally included. As used herein, the term "aryl" refers to a monocyclic or fused bicyclic moiety having the well-known characteristics of aromaticity; examples include phenyl, naphthyl, fluorenyl, and indenyl, which can be optionally substituted. As used herein, the term "hydroxyaryl" refers to an aryl group including one or more hydroxyl groups as substituents; as further detailed below, further substituents can be optionally included. As used herein, the term "heteroaryl" refers to monocyclic or fused bicylic ring systems that have the characteristics of aromaticity and include one or more heteroatoms selected from O, S, and N. The inclusion of a heteroatom permits aromaticity in 5-membered rings as well as in 6-membered rings. Typical heteroaromatic systems include monocyclic $C_5$-$C_6$ heteroaromatic groups such as pyridyl, pyrimidyl, pyrazinyl, thienyl, furanyl, pyrrolyl, pyrazolyl, thiazolyl, oxazolyl, triazolyl, triazinyl, tetrazolyl, tetrazinyl, and imidazolyl, as well as the fused bicyclic moieties formed by fusing one of these monocyclic heteroaromatic groups with a phenyl ring or with any of the heteroaromatic monocyclic groups to form a $C_8$-$C_{10}$ bicyclic group such as indolyl, benzimidazolyl, indazolyl, benzotriazolyl, isoquinolyl, quinolyl, benzothiazolyl, benzofuranyl, pyrazolylpyridyl, quinazolinyl, quinoxalinyl, cinnolinyl, and other ring systems known in the art. Any monocyclic or fused ring bicyclic system that has the characteristics of aromaticity in terms of delocalized electron distribution throughout the ring system is included in this definition. This definition also includes bicyclic groups where at least the ring that is directly attached to the remainder of the molecule has the characteristics of aromaticity, including the delocalized electron distribution that is characteristic of aromaticity. Typically the ring systems contain 5 to 12 ring member atoms and up to four heteroatoms, wherein the heteroatoms are selected from the group consisting of N, O, and S. Frequently, the monocyclic heteroaryls contain 5 to 6 ring members and up to three heteroatoms selected from the group consisting of N, O, and S; frequently, the bicyclic heteroaryls contain 8 to 10 ring members and up to four heteroatoms selected from the group consisting of N, O, and S. The number and placement of heteroatoms in heteroaryl ring structures is in accordance with the well-known limitations of aromaticity and stability, where stability requires the heteroaromatic group to be stable enough to be exposed to water at physiological temperatures without rapid degradation. As used herein, the term "hydroxheteroaryl" refers to a heteroaryl group including one or more hydroxyl groups as substituents; as further detailed below, further substituents can be optionally included. As used herein, the terms "haloaryl" and "haloheteroaryl" refer to aryl and heteroaryl groups, respectively, substituted with at least one halo group, where "halo" refers to a halogen selected from the group consisting of fluorine, chlorine, bromine, and iodine, typically, the halogen is selected from the group consisting of chlorine, bromine, and iodine; as detailed below, further substituents can be optionally included. As used herein, the terms "haloalkyl," "haloalkenyl," and "haloalkynyl" refer to alkyl, alkenyl, and alkynyl groups, respectively, substituted with at least one halo group, where "halo" refers to a halogen selected from the group consisting of fluorine, chlorine, bromine, and iodine, typically, the halogen is selected from the group consisting of chlorine, bromine, and iodine; as detailed below, further substituents can be optionally included.

As used herein, the term "optionally substituted" indicates that the particular group or groups referred to as optionally substituted may have no non-hydrogen substituents, or the group or groups may have one or more non-hydrogen substituents consistent with the chemistry and pharmacological activity of the resulting molecule. If not otherwise specified, the total number of such substituents that may be present is equal to the total number of hydrogen atoms present on the unsubstituted form of the group being described; fewer than the maximum number of such substituents may be present. Where an optional substituent is attached via a double bond, such as a carbonyl oxygen (C=O), the group takes up two available valences on the carbon atom to which the optional substituent is attached, so the total number of substituents that may be included is reduced according to the number of available valences. As used herein, the term "substituted," whether used as part of "optionally substituted" or otherwise, when used to modify a specific group, moiety, or radical, means that one or more hydrogen atoms are, each, independently of each other, replaced with the same or different substituent or substituents.

Substituent groups useful for substituting saturated carbon atoms in the specified group, moiety, or radical include, but are not limited to, $-Z^a$, =O, $-OZ^b$, $-SZ^b$, =S$^-$, $-NZ^cZ^c$, =NZ$^b$, =N$-OZ^b$, trihalomethyl, $-CF_3$, $-CN$, $-OCN$, $-SCN$, $-NO$, $-NO_2$, =N$_2$, $-N_3$, $-S(O)_2Z^b$, $-S(O)_2NZ^b$, $-S(O)_2O^-$, $-S(O)_2OZ^b$, $-OS(O)_2OZ^b$, $-OS(O)_2O^-$, $-OS(O)_2OZ^b$, $-P(O)(O^-)_2$, $-P(O)(OZ^b)(O^-)$, $-P(O)(OZ^b)(OZ^b)$, $-C(O)Z^b$, $-C(S)Z^b$, $-C(NZ^b)Z^b$, $-C(O)O^-$, $-C(O)OZ^b$, $-C(S)OZ^b$, $-C(O)NZ^cZ^c$, $-C(NZ^b)NZ^cZ^c$, $-OC(O)Z^b$, $-OC(S)Z^b$, $-OC(O)O^-$, $-OC(O)OZ^b$, $-OC(S)OZ^b$, $-NZ^bC(O)Z^b$, $-NZ^bC(S)Z^b$, $-NZ^bC(O)O^-$, $-NZ^bC(O)OZ^b$, $-NZ^bC(S)OZ^b$, $-NZ^bC(O)NZ^cZ^c$, $-NZ^bC(NZ^b)Z^b$, $-NZ^bC(NZ^b)NZ^cZ^c$, wherein $Z^a$ is selected from the group consisting of alkyl, cycloalkyl, heteroalkyl, cycloheteroalkyl, aryl, arylalkyl, heteroaryl and heteroarylalkyl; each $Z^b$ is independently hydrogen or $Z^a$; and each $Z^c$ is independently $Z^b$ or, alternatively, the two $Z^c$'s may be taken together with the nitrogen atom to which they are bonded to form a 4-, 5-, 6-, or 7-membered cycloheteroalkyl ring structure which may optionally include from 1 to 4 of the same or different heteroatoms selected from the group consisting of N, O, and S. As specific examples, $-NZ^cZ^c$ is meant to include $-NH_2$, $-NH$-alkyl, $-N$-pyrrolidinyl, and $-N$-morpholinyl, but is not limited to those specific alternatives and includes other alternatives known in the art. Similarly, as another specific example, a substituted alkyl is meant to include -alkylene-O-alkyl, -alkylene-heteroaryl, -alkylene-cycloheteroaryl, -alkylene-C(O)OZ$^b$, -alkylene-C(O)NZ$^b$Z$^b$, and $-CH_2-CH_2-C(O)-CH_3$, but is not limited to those specific alternatives and includes other alternatives known in the art. The one or more substituent groups, together with the atoms to which they are bonded, may form a cyclic ring, including, but not limited to, cycloalkyl and cycloheteroalkyl.

Similarly, substituent groups useful for substituting unsaturated carbon atoms in the specified group, moiety, or radical include, but are not limited to, $-Z^a$, halo, $-O^-$, $-OZ^b$, $-SZ^b$, $-S^-$, $-NZ^cZ^c$, trihalomethyl, $-CF_3$, $-CN$, $-OCN$, $-SCN$, $-NO$, $-NO_2$, $-N_3$, $-S(O)_2Z^b$, $-S(O)_2O^-$, $-S(O)_2OZ^b$, $-OS(O)_2OZ^b$, $-OS(O)_2O^-$, $-P(O)(O^-)_2$, $-P(O)(OZ^b)(O^-)$, $-P(O)(OZ^b)(OZ^b)$, $-C(O)Z^b$, $-C(S)Z^b$, $-C(NZ^b)Z^b$, $-C(O)O^-$, $-C(O)OZ^b$, $-C(S)OZ^b$, $-C(O)NZ^cZ^c$, $-C(NZ^b)NZ^cZ^c$, $-OC(O)Z^b$, $-OC(S)Z^b$, $-OC(O)O^-$, $-OC(O)OZ^b$, $-OC(S)OZ^b$, $-NZ^bC(O)Z^b$, $-NZ^bC(S)Z^b$, $-NZ^bC(O)OZ^b$, $-NZ^bC(S)OZ^b$, $-NZ^bC(O)NZ^cZ^c$, $-NZ^bC(NZ^b)Z^b$, and $-NZ^bC(NZ^b)NZ^cZ^c$, wherein $Z^a$, $Z^b$, and $Z^c$ are as defined above.

Similarly, substituent groups useful for substituting nitrogen atoms in heteroalkyl and cycloheteroalkyl groups include, but are not limited to, $-Z^a$, halo, $-O^-$, $-OZ^b$, $-SZ^b$, $-S^-$, $-NZ^cZ^c$, trihalomethyl, $-CF_3$, $-OCN$, $-SCN$, $-NO$, $-NO_2$, $-S(O)_2Z^b$, $-S(O)_2O^-$, $-S(O)_2OZ^b$, $-OS(O)_2OZ^b$, $-OS(O)_2O^-$, $-P(O)(O^-)_2$, $-P(O)(OZ^b)(O^-)$, $-P(O)(OZ^b)(OZ^b)$, $-C(O)Z^b$, $-C(S)Z^b$, $-C(NZ^b)Z^b$, $-C(O)OZ^b$, $-C(S)OZ^b$, $-C(O)NZ^cZ^c$, $-C(NZ^b)NZ^cZ^c$, $-OC(O)Z^b$, $-OC(S)Z^b$, $-OC(O)OZ^b$, $-OC(S)OZ^b$, $-NZ^bC(O)Z^b$, $-NZ^bC(S)Z^b$, $-NZ^bC(O)OZ^b$, $-NZ^bC(S)OZ^b$, $-NZ^bC(O)NZ^cZ^c$, $-NZ^bC(NZ^b)Z^b$, and $-NZ^bC(NZ^b)NZ^cZ^c$, wherein $Z^a$, $Z^b$, and $Z^c$ are as defined above.

The compounds described herein may contain one or more chiral centers and/or double bonds and therefore, may exist as stereoisomers, such as double-bond isomers (i.e., geometric isomers such as E and Z), enantiomers or diastereomers. The invention includes each of the isolated stereoisomeric forms (such as the enantiomerically pure isomers, the E and Z isomers, and other alternatives for stereoisomers) as well as mixtures of stereoisomers in varying degrees of chiral purity or percentage of E and Z, including racemic mixtures, mixtures of diastereomers, and mixtures of E and Z isomers, unless a specific stereoisomer is specified. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The invention includes each of the isolated stereoisomeric forms as well as mixtures of stereoisomers in varying degrees of chiral purity, including racemic mixtures. It also encompasses the various diastereomers. Other structures may appear to depict a specific isomer, but that is merely for convenience, and is not intended to limit the invention to the depicted isomer. When the chemical name does not specify the isomeric form of the compound, it denotes any one of the possible isomeric forms or mixtures of those isomeric forms of the compound. However, amino acids included in the present invention are L-amino acids unless specifically stated to be D-amino acids.

The compounds may also exist in several tautomeric forms, and the depiction herein of one tautomer is for convenience only, and is also understood to encompass other tautomers of the form shown. Accordingly, the chemical structures depicted herein encompass all possible tautomeric forms of the illustrated compounds. The term "tautomer" as used herein refers to isomers that change into one another with great ease so that they can exist together in equilibrium; the equilibrium may strongly favor one of the tautomers, depending on stability considerations. For example, ketone and enol are two tautomeric forms of one compound.

As used herein, the term "solvate" means a compound formed by solvation (the combination of solvent molecules with molecules or ions of the solute), or an aggregate that consists of a solute ion or molecule, i.e., a compound of the invention, with one or more solvent molecules. When water is the solvent, the corresponding solvate is "hydrate." Examples of hydrate include, but are not limited to, hemihydrate, monohydrate, dihydrate, trihydrate, hexahydrate, and other water-containing species. It should be understood by one of ordinary skill in the art that the pharmaceutically acceptable salt, and/or prodrug of the present compound may also exist in a solvate form. The solvate is typically formed via hydration which is either part of the preparation of the present compound or through natural absorption of moisture by the anhydrous compound of the present invention.

As used herein, the term "ester" means any ester of a present compound in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The hydrolyzable esters of the present compounds are the compounds whose carboxyls are present in the form of hydrolysable ester groups. That is, these esters are pharmaceutically acceptable and can be hydrolyzed to the corresponding carboxyl acid in vivo.

In addition to the substituents described above, alkyl, alkenyl and alkynyl groups can alternatively or in addition be substituted by $C_1$-$C_8$ acyl, $C_2$-$C_8$ heteroacyl, $C_6$-$C_{10}$ aryl, $C_3$-$C_8$ cycloalkyl, $C_3$-$C_8$ heterocyclyl, or $C_5$-$C_{10}$ heteroaryl, each of which can be optionally substituted. Also, in addition, when two groups capable of forming a ring having 5 to 8 ring members are present on the same or adjacent atoms, the two groups can optionally be taken together with the atom or atoms in the substituent groups to which they are attached to form such a ring.

"Heteroalkyl," "heteroalkenyl," and "heteroalkynyl" and the like are defined similarly to the corresponding hydrocarbyl (alkyl, alkenyl and alkynyl) groups, but the "hetero" terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form, respectively, a heteroalkyl, heteroalkenyl, or heteroalkynyl group. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker.

Similarly, "heterocyclyl" may be used to describe a non-aromatic cyclic group that contains at least one heteroatom (typically selected from N, O and S) as a ring member and that is connected to the molecule via a ring atom, which may be C (carbon-linked) or N (nitrogen-linked); and "heterocyclylalkyl" may be used to describe such a group that is connected to another molecule through a linker. The heterocyclyl can be fully saturated or partially saturated, but non-aromatic. The sizes and substituents that are suitable for the cycloalkyl, cycloalkylalkyl, heterocyclyl, and heterocyclylalkyl groups are the same as those described above for alkyl groups. The heterocyclyl groups typically contain 1, 2 or 3 heteroatoms, selected from N, O and S as ring members; and the N or S can be substituted with the groups commonly found on these atoms in heterocyclic systems. As used herein, these terms also include rings that contain a double bond or two, as long as the ring that is attached is not aromatic. The substituted cycloalkyl and heterocyclyl groups also include cycloalkyl or heterocyclic rings fused to an aromatic ring or heteroaromatic ring, provided the point of attachment of the group is to the cycloalkyl or heterocyclyl ring rather than to the aromatic/heteroaromatic ring.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S.

Acyl and heteroacyl groups are bonded to any group or molecule to which they are attached through the open valence of the carbonyl carbon atom. Typically, they are $C_1$-$C_8$ acyl groups, which include formyl, acetyl, pivaloyl, and benzoyl, and $C_2$-$C_8$ heteroacyl groups, which include methoxyacetyl, ethoxycarbonyl, and 4-pyridinoyl.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is $C_1$-$C_8$ alkyl. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a $C_1$-$C_4$ alkylene that is unsubstituted or is substituted with one or two $C_1$-$C_4$ alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a $C_5$-$C_6$ monocyclic heteroaryl group that is optionally substituted with the groups described above as substituents typical on aryl groups and a $C_1$-$C_4$ alkylene that is unsubstituted or is substituted with one or two $C_1$-$C_4$ alkyl groups or heteroalkyl groups, or it includes an optionally substituted phenyl ring or $C_5$-$C_6$ monocyclic heteroaryl and a heteroalkylene that is unsubstituted or is substituted with one or two $C_1$-$C_4$ alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a $C_7$-arylalkyl group, and phenylethyl is a $C_8$-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —$(CH_2)_n$— where n is 1-8 and preferably n is 1-4, though where specified, an alkylene can also be substituted by other groups, and can be of other lengths, and the open valences need not be at opposite ends of a chain.

In general, any alkyl, alkenyl, alkynyl, acyl, or aryl or arylalkyl group that is contained in a substituent may itself optionally be substituted by additional substituents. The nature of these substituents is similar to those recited with regard to the primary substituents themselves if the substituents are not otherwise described.

"Amino" as used herein refers to —$NH_2$, but where an amino is described as "substituted" or "optionally substituted", the term includes NR'R" wherein each R' and R" is independently H, or is an alkyl, alkenyl, alkynyl, acyl, aryl, or arylalkyl group, and each of the alkyl, alkenyl, alkynyl, acyl, aryl, or arylalkyl groups is optionally substituted with the substituents described herein as suitable for the corresponding group; the R' and R" groups and the nitrogen atom to which they are attached can optionally form a 3- to 8-membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, the term "carbocycle," "carbocyclyl," or "carbocyclic" refers to a cyclic ring containing only carbon atoms in the ring, whereas the term "heterocycle" or "heterocyclic" refers to a ring comprising a heteroatom. The carbocyclyl can be fully saturated or partially saturated, but non-aromatic. For example, the carbocyclyl encompasses cycloalkyl. The carbocyclic and heterocyclic structures encompass compounds having monocyclic, bicyclic or multiple ring systems; and such systems may mix aromatic, heterocyclic, and carbocyclic rings. Mixed ring systems are described according to the ring that is attached to the rest of the compound being described.

As used herein, the term "heteroatom" refers to any atom that is not carbon or hydrogen, such as nitrogen, oxygen or sulfur. When it is part of the backbone or skeleton of a chain or ring, a heteroatom must be at least divalent, and will typically be selected from N, O, P, and S.

As used herein, the term "alkanoyl" refers to an alkyl group covalently linked to a carbonyl (C=O) group. The term "lower alkanoyl" refers to an alkanoyl group in which the alkyl portion of the alkanoyl group is $C_1$-$C_6$. The alkyl portion of the alkanoyl group can be optionally substituted as described above. The term "alkylcarbonyl" can alternatively be used. Similarly, the terms "alkenylcarbonyl" and "alkynylcarbonyl" refer to an alkenyl or alkynyl group, respectively, linked to a carbonyl group.

As used herein, the term "alkoxy" refers to an alkyl group covalently linked to an oxygen atom; the alkyl group can be considered as replacing the hydrogen atom of a hydroxyl group. The term "lower alkoxy" refers to an alkoxy group in which the alkyl portion of the alkoxy group is $C_1$-$C_6$. The alkyl portion of the alkoxy group can be optionally substituted as described above. As used herein, the term "haloalkoxy" refers to an alkoxy group in which the alkyl portion is substituted with one or more halo groups.

As used herein, the term "sulfo" refers to a sulfonic acid (—$SO_3H$) substituent.

As used herein, the term "sulfamoyl" refers to a substituent with the structure —$S(O_2)NH_2$, wherein the nitrogen of the $NH_2$ portion of the group can be optionally substituted as described above.

As used herein, the term "carboxyl" refers to a group of the structure —$C(O_2)H$.

As used herein, the term "carbamyl" refers to a group of the structure —$C(O_2)NH_2$, wherein the nitrogen of the $NH_2$ portion of the group can be optionally substituted as described above.

As used herein, the terms "monoalkylaminoalkyl" and "dialkylaminoalkyl" refer to groups of the structure -$Alk_1$-NH-$Alk_2$ and -$Alk_1$-N($Alk_2$)($Alk_3$), wherein $Alk_1$, $Alk_2$, and $Alk_3$ refer to alkyl groups as described above.

As used herein, the term "alkylsulfonyl" refers to a group of the structure —$S(O)_2$-Alk wherein Alk refers to an alkyl group as described above. The terms "alkenylsulfonyl" and "alkynylsulfonyl" refer analogously to sulfonyl groups covalently bound to alkenyl and alkynyl groups, respectively. The term "arylsulfonyl" refers to a group of the structure —$S(O)_2$—Ar wherein Ar refers to an aryl group as described above. The term "aryloxyalkylsulfonyl" refers to a group of the structure —$S(O)_2$-Alk-O—Ar, where Alk is an alkyl group as described above and Ar is an aryl group as described above. The term "arylalkylsulfonyl" refers to a group of the structure —$S(O)_2$-AlkAr, where Alk is an alkyl group as described above and Ar is an aryl group as described above.

As used herein, the term "alkyloxycarbonyl" refers to an ester substituent including an alkyl group wherein the carbonyl carbon is the point of attachment to the molecule. An example is ethoxycarbonyl, which is $CH_3CH_2OC(O)$—. Similarly, the terms "alkenyloxycarbonyl," "alkynyloxycarbonyl," and "cycloalkylcarbonyl" refer to similar ester substituents including an alkenyl group, alkenyl group, or cycloalkyl group respectively. Similarly, the term "aryloxycarbonyl" refers to an ester substituent including an aryl group wherein the carbonyl carbon is the point of attachment to the molecule. Similarly, the term "aryloxyalkylcarbonyl" refers to an ester substituent including an alkyl group wherein the alkyl group is itself substituted by an aryloxy group.

Other combinations of substituents are known in the art and, are described, for example, in U.S. Pat. No. 8,344,162 to Jung et al. For example, the term "thiocarbonyl" and combinations of substituents including "thiocarbonyl" include a carbonyl group in which a double-bonded sulfur replaces the normal double-bonded oxygen in the group. The term "alkylidene" and similar terminology refer to an alkyl group, alkenyl group, alkynyl group, or cycloalkyl group, as specified, that has two hydrogen atoms removed from a single carbon atom so that the group is double-bonded to the remainder of the structure.

The compounds disclosed herein may exist as salts at physiological pH ranges or other ranges. Such salts are described further below. In general, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either net or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either net or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isbutyric, oxalic, maleic, malonic, benzoic, succinic, suberic, fumeric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge, S. M., et al., "Pharmaceutical Salts", Journal of Pharmaceutical Science, 1977, 66, 1-19). Certain specific compounds of the present inventions contain both basic and acidic functionalities that allow the compounds to be converted into either base or acid addition salts.

The pharmaceutical composition according to the present invention can, in some alternatives, include a prodrug. When a pharmaceutical composition according to the present invention includes a prodrug, prodrugs and active metabolites of a compound may be identified using routine techniques known in the art. See, e.g., Bertolini et al., J. Med. Chem., 40, 2011-2016 (1997); Shan et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al., Xenobiol., 3, 103-112 (1992). Further details of prodrugs are described below.

As used herein, the term "prodrug" refers to compounds that are transformed in vivo to yield a disclosed compound or a pharmaceutically acceptable form of the compound. In some embodiments, a prodrug is a compound that may be converted under physiological conditions or by solvolysis to a biologically active compound as described herein. Thus, the term "prodrug" refers to a precursor of a biologically active compound that is pharmaceutically acceptable. A prodrug can be inactive when administered to a subject, but is then converted in vivo to an active compound, for example, by hydrolysis (e.g., hydrolysis in blood or a tissue). In certain cases, a prodrug has improved physical and/or delivery properties over a parent compound from which the prodrug has been derived. The prodrug often offers advantages of solubility, tissue compatibility, or delayed release in a mammalian organism (H. Bundgard, *Design of Prodrugs* (Elsevier, Amsterdam, 1988), pp. 7-9, 21-24), incorporated herein by this reference. A discussion of prodrugs is provided in T. Higuchi et al., "Pro-Drugs as Novel Delivery Systems," *ACS Symposium Series*, Vol. 14 and in E. B. Roche, ed., *Bioreversible Carriers in Drug Design* (American Pharmaceutical Association & Pergamon Press, 1987), both incorporated herein by this reference. Exemplary advantages of a prodrug can include, but are not limited to, its physical properties, such as enhanced water solubility for parenteral administration at physiological pH compared to the parent compound, enhanced absorption from the digestive tract, or enhanced drug stability for long-term storage.

The term "prodrug" is also meant to include any covalently bonded carriers which release the active compound in vivo when the prodrug is administered to a subject. Prodrugs of a therapeutically active compound, as described herein, can be prepared by modifying one or more functional groups present in the therapeutically active compound in such a way that the modifications are cleaved, either in routine manipulation or in vivo, to yield the parent therapeutically active compound. Prodrugs include compounds wherein a hydroxy, amino, or mercapto group is covalently bonded to any group that, when the prodrug of the active compound is administered to a subject, cleaves to form a free hydroxy, free amino, or free mercapto group, respectively. Examples of prodrugs include, but are not limited to, formate or benzoate derivatives of an alcohol or acetamide, formamide or benzamide derivatives of a therapeutically active agent possessing an amine functional group available for reaction, and the like.

For example, if a therapeutically active agent or a pharmaceutically acceptable form of a therapeutically active agent contains a carboxylic acid functional group, a prodrug can comprise an ester formed by the replacement of the hydrogen atom of the carboxylic acid group with a group such as $C_{1-8}$ alkyl, $C_{2-12}$ alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, γ-butyrolacton-4-yl, di-N,N($C_1$-$C_2$)alkylamino($C_2$-$C_3$)alkyl (such as (3-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino-, or morpholino($C_2$-$C_3$)alkyl.

Similarly, if a disclosed compound or a pharmaceutically acceptable form of the compound contains an alcohol functional group, a prodrug can be formed by the replacement of the hydrogen atom of the alcohol group with a group such as ($C_1$-$C_6$)alkanoyloxymethyl, 1-(($C_1$-$C_6$))alkanoyloxy) ethyl, 1-methyl-1-(($C_1$-$C_6$)alkanoyloxy)ethyl ($C_1$-$C_6$) alkoxycarbonyloxymethyl, N($C_1$-$C_6$)alkoxycarbonylaminomethyl, succinoyl, ($C_1$-$C_6$)alkanoyl, α-amino($C_1$-$C_4$) alkanoyl, arylacyl and α-aminoacyl, or α-aminoacyl-α-aminoacyl, where each α-aminoacyl group is independently selected from the naturally occurring L-amino acids, P(O) (OH)$_2$, P(O)(O($C_1$-$C_6$)alkyl)$_2$ or glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl-natural α-aminoacyl, C(OH)C(O)OY$^1$ wherein Y$^1$ is H, ($C_1$-$C_6$)alkyl or benzyl, C(OY$^2$)Y$^3$ wherein Y$^2$ is ($C_1$-$C_4$) alkyl and Y$^3$ is ($C_1$-$C_6$)alkyl, carboxy($C_1$-$C_6$) alkyl, amino($C_1$-$C_4$)alkyl or mono-N or di-N,N($C_1$-$C_6$)alkylaminoalkyl, C(Y$^4$)Y$^5$ wherein Y$^4$ is H or methyl and Y$^5$ is mono-N or di-N,N($C_1$-$C_6$)alkylamino, morpholino, piperidin-1-yl or pyrrolidin-1-yl.

The use of prodrug systems is described in T. Järvinen et al., "Design and Pharmaceutical Applications of Prodrugs" in *Drug Discovery Handbook* (S. C. Gad, ed., Wiley-Interscience, Hoboken, N.J., 2005), ch. 17, pp. 733-796, incorporated herein by this reference.

When a pharmacologically active compound according to the present invention possesses a sufficiently acidic, a sufficiently basic, or both a sufficiently acidic and a sufficiently basic functional group, these group or groups can accordingly react with any of a number of inorganic or organic bases, and inorganic and organic acids, to form a pharmaceutically acceptable salt. Exemplary pharmaceutically acceptable salts include those salts prepared by reaction of the pharmacologically active compound with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propionates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, β-hydroxybutyrates, glycolates, tartrates, methane-sulfonates, propanesulfonates, naphthalene-1-sulfonates, naphthalene-2-sulfonates, and mandelates. If the pharmacologically active compound has one or more basic functional groups, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the pharmacologically active compound has one or more acidic functional groups, the desired pharmaceutically acceptable salt may be prepared by any suitable method available in the art, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

IX. Pharmaceutical Compositions

Another aspect of the present invention is a pharmaceutical composition that is useful for the treatment of a psychiatric or psychological condition as described above. In general, a pharmaceutical composition according to the present invention comprises: (1) at least one therapeutically active agent for the treatment of a psychiatric or psychological disease or condition as described above; and (2) a pharmaceutically acceptable carrier or excipient.

The at least one therapeutically active agent for treatment of a psychiatric or psychological condition can be: (i) a derivative of phyllokinin as described above; (ii) L-tryptophan or a derivative or analog thereof as described above; (iii) a derivative of phyllokinin and an additional agent for treatment of a psychiatric or psychological disease or condition, such as an antidepressant as described above; (iv) L-tryptophan or a derivative or analog thereof and an additional agent for treatment of a psychiatric or psychological disease or condition; (v) a derivative of phyllokinin and L-tryptophan or a derivative or analog thereof; or (vi) a derivative of phyllokinin, L-tryptophan or a derivative or analog thereof, and an additional agent for treatment of a psychiatric or psychological disease or condition.

Typically, the active compound that is a phyllokinin derivative is a peptide of SEQ ID NO: 11 with nine carboxyl-terminal tryptophan residues. Typically, the active compound that is L-tryptophan or a derivative or analog of L-tryptophan is L-tryptophan. Typically, the pharmaceutical composition is formulated for treatment of depression.

Typically, the pharmaceutical composition is formulated for subcutaneous administration. However, in other alternatives, the pharmaceutical composition can be formulated for administration by a route selected from the group consisting of intravenous administration, intraperitoneal, and intramuscular administration.

The compositions of the invention may be manufactured using techniques generally known for preparing pharmaceutical compositions, e.g., by conventional techniques such as mixing, dissolving, granulating, dragee-making, levitating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations, which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

Typically, the at least one pharmaceutically acceptable excipient is selected from the group consisting of: a liquid carrier; an isotonic agent; a wetting, solubilizing, or emulsifying agent; a preservative; a buffer; an acidifying agent; an antioxidant; an alkalinizing agent; a carrying agent; a chelating agent; a colorant; a complexing agent; a solvent; a suspending and/or viscosity-increasing agent; an oil; a penetration enhancer; a polymer; a stiffening agent; a thickening agent; a protein; a carbohydrate; a bulking agent; and a lubricating agent. Pharmaceutically acceptable excipients may be added to facilitate manufacture, enhance stability, control release, enhance product characteristics, enhance bioavailability, drug absorption or solubility, optimize other pharmacokinetic considerations, optimize the pharmaceutical formulation for a route of administration, enhance patient acceptability, or for another reason related to manufacture, storage, or use of a pharmaceutical composition. Excipients used in pharmaceutical compositions according to the present invention are compatible with the pharmaceutically active agent or agents included in the pharmaceutical composition, are compatible with other excipients included in the pharmaceutical composition, and are not injurious to and are tolerated by any patients to whom the pharmaceutical composition is administered.

As is generally known in the art of pharmaceutical formulation, a particular excipient can fulfill one or more of these functions in a particular pharmaceutical composition, depending on the concentration of the excipient, the other excipients in the composition, the physical form of the composition, the concentration of active agent in the composition, the intended route of administration of the composition, and other factors. The recitation of a particular excipient in a category below is not intended to exclude the possible use of the excipient in another category or categories.

Typically, the liquid carrier can be, but is not limited to, a liquid carrier selected from the group consisting of saline, phosphate buffered saline, glycerol, and ethanol.

Typically, the isotonic agent can be, but is not limited to, a polyalcohol selected from the group consisting of mannitol and sorbitol, sodium chloride, and potassium chloride.

Typically, the wetting or emulsifying agent is a surfactant. Typically, the surfactant is selected from the group consisting of benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol, acacia, cholesterol, diethanolamine, glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, triethanolamine, emulsifying wax, cetomacrogol, and cetyl alcohol.

Typically, the preservative is selected from the group consisting of benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, diazolidinyl urea, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, and thymol.

Typically, the buffer is selected from the group consisting of acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate, sodium bicarbonate, Tris (Tris(hydroxymethyl)aminomethane), MOPS (3-(N-morpholino) propanesulfonic acid), HEPES (N-(2-hydroxyethyl)piperazine-N'-(2-ethanesulfonic acid), ACES (2-[(2-amino-2-oxoethyl)amino]ethanesulfonic acid), ADA (N-(2-acetamido)$_2$-iminodiacetic acid), AMPSO (3-[(1,1-dimethyl-2-hydroxyethylamino]-2-propanesulfonic acid), BES (N,N-bis(2-hydroxyethyl)-2-aminoethanesulfonic acid, Bicine (N,N-bis(2-hydroxyethylglycine), Bis-Tris (bis-(2-hydroxyethyl)imino-tris(hydroxymethyl)methane, CAPS (3-(cyclohexylamino)-1-propanesulfonic acid), CAPSO (3-(cyclohexylamino)-2-hydroxy-1-propanesulfonic acid), CHES (2-(N-cyclohexylamino)ethanesulfonic acid), DIPSO (3-[N,N-bis(2-hydroxyethylamino]-2-hydroxy-propane-sulfonic acid), HEPPS (N-(2-hydroxyethylpiperazine)-N'-(3-propanesulfonic acid), HEPPSO (N-(2-hydroxyethyl) piperazine-N'-(2-hydroxypropanesulfonic acid), MES (2-(N-morpholino)ethanesulfonic acid), triethanolamine, imidazole, glycine, ethanolamine, phosphate, MOPSO (3-(N-morpholino)-2-hydroxypropanesulfonic acid), PIPES (piperazine-N,N'-bis(2-ethanesulfonic acid), POPSO (piperazine-N, N'-bis(2-hydroxypropaneulfonic acid), TAPS (N-tris[hydroxymethyl)methyl-3-aminopropanesulfonic acid), TAPSO (3-[N-tris(hydroxymethyl)methylamino]-2-hydroxy-propanesulfonic acid), TES (N-tris(hydroxymethyl)methyl-2-aminoethanesulfonic acid), tricine (N-tris (hydroxymethyl)methylglycine), 2-amino-2-methyl-1,3-propanediol, and 2-amino-2-methyl-1-propanol.

Typically, the acidifying agent is selected from the group consisting of acetic acid, citric acid, fumaric acid, hydrochloric acid, diluted hydrochloric acid, malic acid, nitric acid, phosphoric acid, diluted phosphoric acid, sulfuric acid, and tartaric acid.

Typically, the antioxidant is selected from the group consisting of ascorbic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate, sodium metabisulfite, sodium thiosulfate, sulfur dioxide, and tocopherol.

Typically, the alkalinizing agent is selected from the group consisting of strong ammonia solution, ammonium carbonate, diethanolamine, diisopropanolamine, potassium hydroxide, sodium bicarbonate, sodium borate, sodium carbonate, sodium hydroxide, and trolamine.

Typically, the carrying agent is selected from the group consisting of acacia syrup, aromatic syrup, aromatic elixir, cherry syrup, cocoa syrup, orange syrup, syrup, corn oil, mineral oil, peanut oil, sesame oil, bacteriostatic sodium chloride for injection and bacteriostatic water for injection.

Typically, the chelating agent is selected from the group consisting of edetate disodium, ethylenediaminetetraacetic acid, citric acid, and salicylates.

Typically, the coloring agent is selected from the group consisting of ferric oxides red, yellow, black or blends, FD&C Red No. 3, FD&C Red No. 20, FD&C Yellow No. 6, FD&C Blue No. 2, D&C Green No. 5, D&C Orange No. 5, D&C Red No. 8, and dyes suitable for pharmaceutical use.

Typically, the complexing agent is selected from the group consisting of ethylenediaminetetraacetic acid, salts of ethylenediaminetetraacetic acid, gentisic acid ethanolamide, and oxyquinoline sulfate.

Typically, the solvent is selected from the group consisting of acetone, ethanol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl isobutyl ketone, mineral oil, oleic acid, peanut oil, polyethylene glycol, propylene carbonate, propylene glycol, sesame oil, water for injection, sterile water for injection, sterile water for irrigation, and purified water.

Typically, the suspending and/or viscosity-increasing agent is selected from the group consisting of acacia, agar, alginic acid, aluminum monostearate, bentonite, purified bentonite, magma bentonite, carbomers, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, Veegum, and xanthan gum.

Typically, the oil is selected from the group consisting of arachis oil, mineral oil, olive oil, sesame oil, cottonseed oil, safflower oil, corn oil, and soybean oil.

Typically, the penetration enhancer is selected from the group consisting of monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones, and ureas.

Typically, the polymer is selected from the group consisting of cellulose acetate, alkyl celluloses, hydroxyalkylcelluloses, acrylic polymers and copolymers, polyesters, polycarbonates, and polyanhydrides.

Typically, the stiffening agent is selected from the group consisting of hydrogenated castor oil, cetostearyl alcohol, cetyl alcohol, cetyl esters wax, hard fat, paraffin, polyethylene excipient, stearyl alcohol, emulsifying wax, white wax, and yellow wax.

Typically, the protein is selected from the group consisting of bovine serum albumin, human serum albumin (HSA), recombinant human albumin (rHA), gelatin, and casein.

Typically, the carbohydrate is selected from the group consisting of fructose, maltose, galactose, glucose, D-mannose, sorbose, lactose, sucrose, trehalose, cellobiose, raffinose, melezitose, maltodextrins, dextrans, starches, mannitol, maltitol, lactitol, xylitol, sorbitol, and myoinositol.

Typically, the bulking agent is selected from the group consisting of polypeptides and amino acids.

Typically, the lubricating agent is selected from the group consisting of magnesium stearate, stearic acid, sodium lauryl sulfate, and talc.

Excipients for a pharmaceutical composition according to the present invention are selected such that they do not interfere with the activity of the therapeutic agent or agents that are included in the pharmaceutical composition. Excipients for a pharmaceutical composition according to the present invention are also selected so that they do not interfere with the activity of other excipients or cause phase separation in the composition. In general, when a hydrophobic excipient such as an oil is included in the composition, a surfactant, wetting agent, or emulsifier is also included in the composition to ensure that phase separation does not occur and to ensure that composition remains stable and homogeneous. The quantities of any excipient included in a composition according to the present invention can be determined by one of ordinary skill in the art in order to ensure suitable physical properties of the composition and also in order to ensure suitable pharmacokinetics for the active therapeutic agent or agents included in the composition.

Yet another aspect of the present invention is a kit comprising, separately packaged: (1) two or more unit doses of L-tryptophan or a derivative or analog thereof as described above; (2) two or more unit doses of a derivative of phyllokinin as described above; and (3) instructions for use. The unit doses of L-tryptophan or a derivative or analog thereof and the unit doses of the derivative of phyllokinin can be the same or different dosages of the therapeutically active agents. Typically, the unit doses are formulated for subcutaneous administration and are packaged in conventional packaging, such as ampules.

ADVANTAGES OF THE INVENTION

The present invention provides methods and compositions suitable for treatment of psychiatric and psychological diseases and conditions, including, but not limited to, depression. The methods and compositions according to the present invention are well tolerated and can be used together with antidepressants or other pharmacological or non-pharmacological methods of treating such diseases and conditions.

As used herein in the specification and claims, the term "comprising" and equivalent language also encompasses the terms "consisting essentially of" and "consisting of" with respect to the scope of any claims presented herein.

Methods according to the present invention possess industrial applicability for the preparation of a medicament for the treatment of psychiatric or psychological diseases and conditions, including, but not limited to, depression. Compositions according to the present invention possess industrial applicability as pharmaceutical compositions, particularly for the treatment of psychiatric or psychological diseases and conditions, including, but not limited to, depression.

The method claims of the present invention provide specific method steps that are more than general applications of laws of nature and require that those practicing the method steps employ steps other than those conventionally known in the art, in addition to the specific applications of laws of nature recited or implied in the claims, and thus confine the scope of the claims to the specific applications recited therein. In some contexts, these claims are directed to new ways of using an existing drug.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

What is claimed is:

1. A pharmaceutical composition comprising a phyllokinin derivative for the treatment of a psychiatric or psychological disease or condition, wherein the phyllokinin derivative has the structure selected from the group consisting of:

(a) Arg-Pro-Pro-Gly-Phe-Ser-Pro-Phe-Arg-Trp (SEQ ID NO: 3);

(b) Arg-Pro-Pro-Gly-Phe-Ser-Pro-Phe-Arg-Trp-Trp (SEQ ID NO: 4);

(c) Arg-Pro-Pro-Gly-Phe-Ser-Pro-Phe-Arg-Trp-Trp-Trp (SEQ ID NO: 5);

(d) Arg-Pro-Pro-Gly-Phe-Ser-Pro-Phe-Arg-Trp-Trp-Trp-Trp (SEQ ID NO: 6);

(e) Arg-Pro-Pro-Gly-Phe-Ser-Pro-Phe-Arg-Trp-Trp-Trp-Trp-Trp (SEQ ID NO: 7);

(f) Arg-Pro-Pro-Gly-Phe-Ser-Pro-Phe-Arg-Trp-Trp-Trp-Trp-Trp-Trp (SEQ ID NO: 8);

(g) Arg-Pro-Pro-Gly-Phe-Ser-Pro-Phe-Arg-Trp-Trp-Trp-Trp-Trp-Trp-Trp (SEQ ID NO: 9);

(h) Arg-Pro-Pro-Gly-Phe-Ser-Pro-Phe-Arg-Trp-Trp-Trp-Trp-Trp-Trp-Trp-Trp (SEQ ID NO: 10);

(i) Arg-Pro-Pro-Gly-Phe-Ser-Pro-Phe-Arg-Trp-Trp-Trp-Trp-Trp-Trp-Trp-Trp-Trp (SEQ ID NO: 11);

(j) Arg-Pro-Pro-Gly-Phe-Ser-Pro-Phe-Arg-Trp-Trp-Trp-Trp-Trp-Trp-Trp-Trp-Trp-Trp (SEQ ID NO: 12); and (ii) a pharmaceutically acceptable excipient; wherein the psychiatric or psychological disease or condition is selected from the group consisting of depression, anxiety, post-traumatic stress disorder, bipolar disorder, substance abuse disorder, eating disorders, obsessive-compulsive disorder, and dysphoria.

2. A pharmaceutical composition for the treatment of a psychiatric or psychological disease or condition comprising: (i) a phyllokinin derivative, wherein the phyllokinin derivative has the structure of SEQ ID NO: 2 extended at its carboxyl-terminus with from 11 to 100 tryptophan residues; with from 100 to 1000 tryptophan residues; or with from 1000 to 100,000 tryptophan residues; and (ii) a pharmaceutically acceptable excipient; wherein the psychiatric or psychological disease or condition is selected from the group consisting of depression, anxiety, post-traumatic stress disorder, bipolar disorder, substance abuse disorder, eating disorders, obsessive-compulsive disorder, and dysphoria.

3. A pharmaceutical composition comprising: (a) at least one therapeutically active agent for the treatment of a psychiatric or psychological disease or condition, wherein the at least one therapeutically active agent is a phyllokinin derivative, and wherein the phyllokinin derivative has the structure selected from the group consisting of:
(i) H-D-Arg-Arg-Pro-Hyp-Gly-Thi-Ser-D-BT-Arg-OH (SEQ ID NO: 14);
(ii) H-Arg-Pro-Pro-Gly-Phe-Ser-D-BT-Arg-OH (SEQ ID NO: 15);
(iii) H-Arg-Pro-Hyp-Gly-Thi-Ser-Pro-4-Me-Tyrψ(CH$_2$NH)-Arg-OH (SEQ ID NO: 16);
(iv) D-Arg-Arg-Pro-Hyp-Gly-Igl-Ser-Oic-Igl-Arg-TFA (SEQ ID NO: 17);
(v) H-D-Arg-Arg-Pro-Hyp-Gly-Thi-Ser-D-Tic-Oic-Arg-OH (SEQ ID NO: 18);
(vi) Met-Lys-Arg-Pro-Pro-Gly-Phe-Ser-Pro-Phe-Arg (SEQ ID NO: 19);
(vii) Ile-Ser-Arg-Pro-Pro-Gly-Phe-Ser-Pro-Phe-Arg (SEQ ID NO: 20);
(viii) Arg-Pro-Hyp-Gly-Phe-Ser-Pro-Phe-Arg (SEQ ID NO: 21);
(ix) Asp-Leu-Pro-Lys-Ile-Asn-Arg-Lys-Gly-Pro-Arg-Pro-Pro-Gly-Phe-Ser-Pro-Phe-Arg (SEQ ID NO: 22); and
(x) Phe-Arg-Ala-Asp-His-Phe-Pro-Leu (SEQ ID NO: 23); and
(b) a pharmaceutically acceptable excipient; wherein the psychiatric or psychological disease or condition is selected from the group consisting of depression, anxiety, post-traumatic stress disorder, bipolar disorder, substance abuse disorder, eating disorders, obsessive-compulsive disorder, and dysphoria.

4. A pharmaceutical composition comprising:
(a) at least one therapeutically active agent for the treatment of a psychiatric or psychological disease or condition, wherein the at least one therapeutically active agent is a phyllokinin derivative, and wherein the phyllokinin derivative is a peptide derived from the peptide of SEQ ID NO: 13 to SEQ ID NO: 23 by the addition of from 1 to 100 tryptophan residues at their carboxyl-termini; from 100 to 1000 tryptophan residues at their carboxyl-termini; or from 1000 to 100,000 tryptophan residues at their carboxyl-termini; and
(b) a pharmaceutically acceptable excipient;
wherein the psychiatric or psychological disease or condition is selected from the group consisting of depression, anxiety, post-traumatic stress disorder, bipolar disorder, substance abuse disorder, eating disorders, obsessive-compulsive disorder, and dysphoria.

5. A pharmaceutical composition comprising:
(a) at least one therapeutically active agent for the treatment of a psychiatric or psychological disease or condition, wherein the at least one therapeutically active agent is a phyllokinin derivative, and wherein the phyllokinin derivative is a bradykinin analog of Formula (X) (SEQ ID NO. 25):

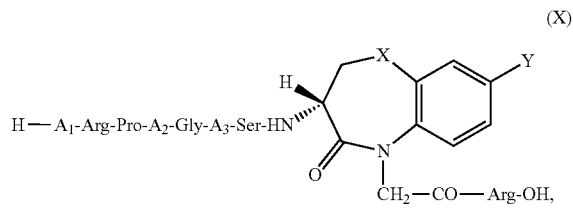

wherein:
(1) $A_1$ is a single bond, D-Arg, or L-Lys;
(2) $A_2$ is L-Pro or trans-4-hydroxy-L-Pro;
(3) $A^3$ is L-Phe or L-thienylalanine;
(4) Y is a hydrogen atom or $C_1$-$C_3$ alkyl; and
(5) X is a sulfur or oxygen atom; and
(b) a pharmaceutically acceptable excipient;
wherein the psychiatric or psychological disease or condition is selected from the group consisting of depression, anxiety, post-traumatic stress disorder, bipolar disorder, substance abuse disorder, eating disorders, obsessive-compulsive disorder, and dysphoria.

6. A pharmaceutical composition comprising:
(a) at least one therapeutically active agent for the treatment of a psychiatric or psychological disease or condition, wherein the at least one therapeutically active agent is L-tryptophan or a derivative or analog thereof, and wherein the tryptophan or derivative or analog thereof is tryptophan, and wherein the composition comprises a derivative of phyllokinin; and
(b) a pharmaceutically acceptable excipient;
wherein the psychiatric or psychological disease or condition is selected from the group consisting of depression, anxiety, post-traumatic stress disorder, bipolar disorder, substance abuse disorder, eating disorders, obsessive-compulsive disorder, and dysphoria.

7. A pharmaceutical composition for the treatment of a psychiatric or psychological disease or condition wherein the pharmaceutical composition comprises:
(a) L-tryptophan; and
(b) a phyllokinin derivative of the structure Arg-Pro-Pro-Gly-Phe-Ser-Pro-Phe-Arg-Trp-Trp-Trp-Trp-Trp-Trp-Trp-Trp-Trp (SEQ ID NO: 11); and
(c) a pharmaceutically acceptable excipient.

8. A kit comprising, separately packaged:
(a) two or more unit doses of L-tryptophan or a derivative or analog thereof;
(b) two or more unit doses of a derivative of phyllokinin, wherein the derivative of phyllokinin is a phyllokinin derivative of the structure Arg-Pro-Pro-Gly-Phe-Ser-Pro-Phe-Arg-Trp-Trp-Trp-Trp-Trp-Trp-Trp-Trp-Trp (SEQ ID NO: 11); and
(c) instructions for use.

* * * * *